United States Patent [19]

Schmidt et al.

[11] Patent Number: 5,243,517

[45] Date of Patent: Sep. 7, 1993

[54] METHOD AND APPARATUS FOR PHYSIOLOGICAL EVALUATION OF SHORT FILMS AND ENTERTAINMENT MATERIALS

[75] Inventors: Albert L. Schmidt, Murrysville; Ellen K. McKinley, Monroeville; Gary W. Sherwin, East Huntingdon Township, Westmoreland County; Lewis F. Hanes, Mt. Lebanon Township, Allegheny County, all of Pa.

[73] Assignee: Westinghouse Electric Corp., Pittsburgh, Pa.

[21] Appl. No.: 228,136

[22] Filed: Aug. 3, 1988

[51] Int. Cl.$^5$ .............. G06F 15/38; G06F 15/00; G09B 19/00; A61B 5/04
[52] U.S. Cl. .............. 364/419.2; 364/413.05; 434/236; 128/731; 351/210
[58] Field of Search .............. 434/236; 128/731, 745; 351/210; 354/62; 364/419, 413.05

[56] References Cited

U.S. PATENT DOCUMENTS

| | | | |
|---|---|---|---|
| 4,483,681 | 11/1984 | Weinblatt | 434/236 |
| 4,528,989 | 7/1985 | Weinblatt | 128/745 |
| 4,755,045 | 6/1988 | Borah et al. | 354/62 |
| 4,781,596 | 11/1988 | Weinblatt | 434/236 |
| 4,789,235 | 12/1988 | Borah et al. | 351/210 |
| 4,794,533 | 12/1988 | Cohen | 128/731 |

OTHER PUBLICATIONS

Appel, V., Weinstein, S. & Weinstein, C. Brain activity and recall of TV advertising Journal of Advertising Research 19(4), 1979.

Begleiter, H. & Platz, H. Cortical evoked potentials to semantic stimuli. Physiological Psychology, 6, 91–100, 1969.

Bentin, S., McCarthy, G., & Wood, C. C. Event-related potentials, lexical decision and semantic priming. Electroencephalography and Clinical Neurophysiology, 60, 343–355, 1985.

Chapman, R. M. McCrary, J. W., Chapman, J. A. & Bragdon, H. R. Brain responses related to semantic meaning. Brain and Language, 5, 195–205 1978.

Cohen, R. J. Overbiew of emerging evaluative and diagnostic methods. Paper presented at the Fourth Annual ARF Copy Research Workshop, New York, May 19–20, 1987.

Collins, A. M., & Quillian, M. R. A spreading activation theory of semantic processing. Psychological Review, 82, 407, 428, 1975.

(List continued on next page.)

*Primary Examiner*—Donald E. McElheny, Jr.
*Assistant Examiner*—Xuong M. Chung
*Attorney, Agent, or Firm*—M. P. Lynch

[57] ABSTRACT

The present invention uses a personal computer 180 with an A/D converter 184 and a hard disk drive 182 to record the electroencephalographic (EEG) activity of a subject 192 during a commercial and to record event related potentials (ERP) during commercial evaluation sequences subsequent to the commercial. The EEG is analyzed by a signal processing computer 205 for alpha and beta frequency amplitude content to determine attention cognition of the commercial. Different commercials for the same product are compared using overall attention and cognition ratings. The ERP is analyzed to determine the amplitude and latency of the ERPs potentials produced by stimulus events in the evaluation sequences. The ERPs are filtered and the peak amplitudes and latency measured. The amplitude and/or latency determines the understanding of the commercial, the value of the product, the intent to buy the product and the memory of the product. By computing overall results for each commercial different commercials can be compared. The effectiveness the commercial can be compared to a reference product and a well known local price providing additional information concerning the product to the advertiser.

16 Claims, 17 Drawing Sheets

Microfiche Appendix Included
(14 Microfiche, 1 Pages)

OTHER PUBLICATIONS

Recognition and surprise alter the human evoked response. Proc. Natl. Sci. 79, 2121-2123, 1982.

Ray W. R. & Cole, H. W. EEG Alpha activity reflects attentional demands, and Beta activity reflects emotional and cognitive processes. Science, 228, 750-752, 1985.

Rugg, M. D. The effects of semantic priming and word repetition on event-related potentials. Psychophysiology, 22(6), 642-647, 1985.

Sanquist, T. F., Rohrbaugh, J. W., Syndulko, D. & Lindsley, D. B. Electrocortical signs of levels of processing: Perceptual analysis and recognition memory. Psychophysiology, 17, 568-576, 1980.

Shagass, C. Electrical activity of the brain. In N. S. Greenfield & R. A. Sternbach (Eds.) Handbook of Psychophysiology, New York: Holt, Rinehart and Winston, 1972.

Smith, E. E., Shoben, E. J. & Rips, L. J. Structure and process in semantic memory: A featural model for semantic decision. Psychological Review, 81, 214, 241, 1974.

Warren, R. E. Time and the spread of activation in memory. Journal of Experimental Psychology: Learning and Memory, 3(4), 449-466, 1977.

Donchin, E., Karis, D., Bashore, T. T., Coles, M. G. H. & Gratton, G. Cognitive psychophysiology and human information processing. In. M. G. H. Coles, E. Donchin, S. W. Porges (Eds.) Psychophysiology Systems Processes, and Applications. New York: Guilford Press, 1986.

Donchin, E. Ritter, W. R., & McCallum, C. In E. Callaway & S. Koslow (Eds.), Event related brain potentials in man. New York: Academic Press, 1978.

Galin D. & Ornestein, R. Lateral specialization of cognitive mode: An EEG study. Psychophysiology, 9(4), 412-418, 1972.

Gevins, A. S., Zeitlin, G. M., Yingling, C. D., Doyle, J. C., Dedon, M. F., Schaffer, R. E., Roumasset, J. T., & Yeager, C. L. EEG patterns during 'cognitive' tasks. I. Methodology and analysis of complex behaviors. Electroencephalography and Clinical neurophysiology, 47, 693-703, 1979.

Harman D. & Ray, W. J. Hemispheric activity during affective verbal stimuli: An EEG study. Neuropsychologia, 15, 457-460, 1977.

Hillyard, S. A. & Kutas, M. Electrophysiology of cognitive processing. Annual review of Psychology, 34, 33-61, 1983.

Karis, D., Fabiani, M. & Donchin, E. "P300" and memory: Individual differences in the von Restorff effect. Cognitive Psychology, 16, 177 218, 1984.

Kutas, M. & Hillyard, S. A. Brain potentials during reading reflect word expectancy and semantic association. Nature, 307, 161-163, 1984.

Neville, H. J., Kutas, M., Chesney, G. & Schmidt, A. L. Event-related brain potentials during initial encoding and recognition memory of cogruous and incongruous words. Journal of Memory and Language. 25, 75-92, 1986.

Neville, H., Snyder, E., Woods, D. D. & Galambos, R.

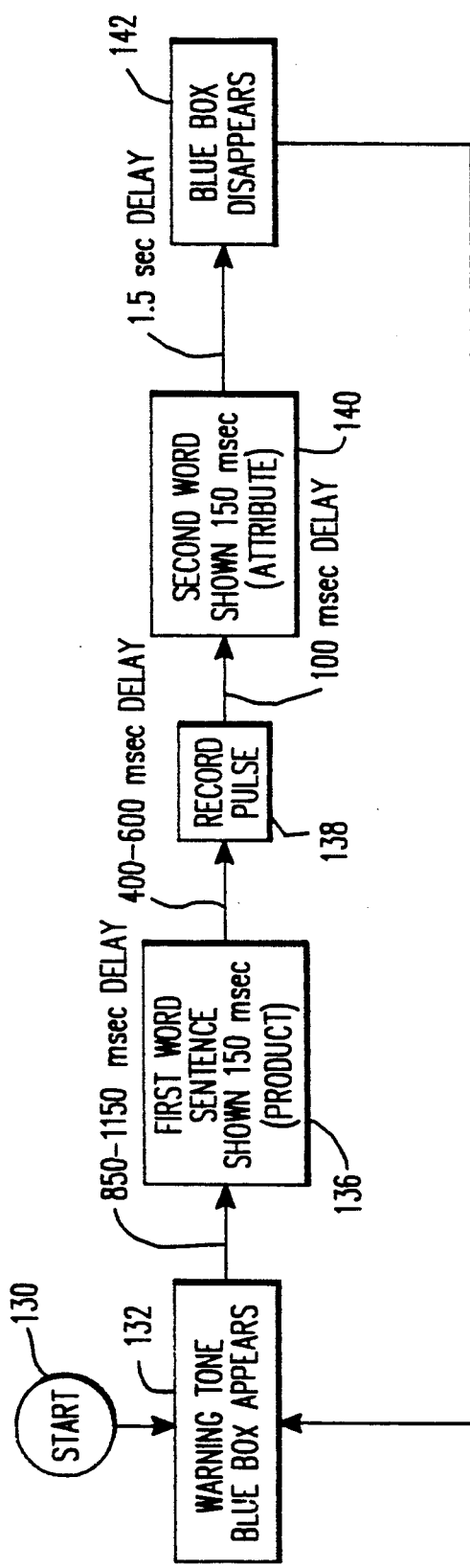
FIG. 16
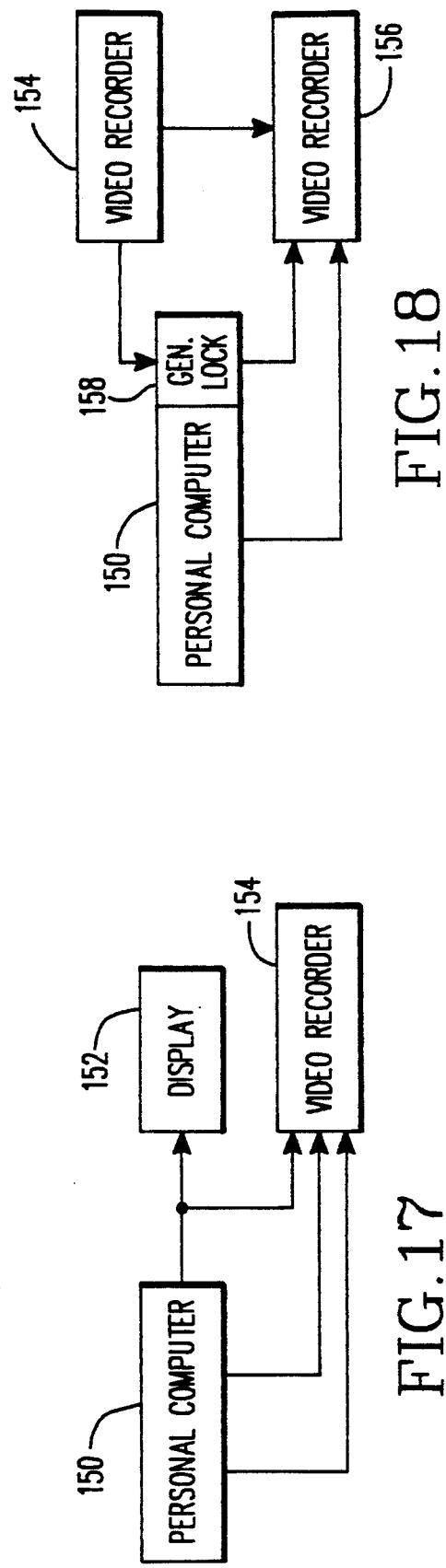
FIG. 18
FIG. 17

METHOD AND APPARATUS FOR PHYSIOLOGICAL EVALUATION OF SHORT FILMS AND ENTERTAINMENT MATERIALS

MICROFICHE APPENDIX

A microfiche appendix containing one fiche and 14 frames is incorporated herein and includes computer program pseudocode listings referenced as Appendices 1, 3 and 4 and video sequence control script referenced as Appendix 2.

BACKGROUND OF THE INVENTION

1. Field of the Invention

The present invention is directed to an objective technique for evaluating short films particularly television advertisements and, more particularly, to a computerized technique for recording and analyzing the electrical activity of a subject's brain during the advertisement to determine attention to and cognition of the advertisement and event related potential recording during test sessions subsequent to the advertisement to determine the subjects understanding of the advertisement, memory of the advertisement product, perceived value of the product and intent to buy the product.

2. Description of the Related Art

Previous methods of evaluating the effects of television advertisements have involved either paper and pencil behavioral methods or physiological methods. Subjective interviews, paper and pencil surveys and day after recall have not proven to be reliable or valid methods of measuring and predicting the effect of an advertisement on current and future consumer attitudes and behavior. These methods of measuring the impact of an advertisement have not been as successful as desired because consumers become confused by requests to self-report their feelings and thoughts and often respond by giving answers they feel are socially correct or expected. Secondly, the self-reporting always lacks "objectivity". Objective physiological measures, galvanic, skin response, heart rate, pupil dilation, and the electroencephalogram (EEG) have been used to evaluate the effect of an advertisement as described in Appel et al., "Brain Activity and Recall of TV Advertising", Journal of Advertising Research; 19(4), 1979. These efforts have been criticized on the basis that they tend to measure general arousal and that the responses toward the commercial could not be verified as the subject's reaction to the commercial or some other external stimuli. In addition, these physiological measures lacked an affective direction, that is, the methods do not indicate whether a positive or negative reaction to the commercial is being exhibited.

SUMMARY OF THE INVENTION

It is an object of the present invention to objectively determine the effect of a short film, such as a television commercial, on a subject.

It is another object of the present invention to provide a system that will allow the effect of a television commercial to be evaluated automatically.

It is also an object of the invention to determine attention to and cognition of a commercial and awareness of the commercial product, understanding of the message of the commercial, as well as the perceived value of the product and intent to buy the product.

It is a further object of the present invention to evaluate attention and cognition associated with entertainment material such as movies and television programs.

The above objects can be attained using a computer to record the electrical activity of a subject's brain while the subject is viewing a commercial and during commercial evaluation sequences subsequent to the commercial. The electroencephalographic (EEG) activity recorded during the commercial is analyzed for frequency content to determine attention to and cognition of the commercial. The electrical brain activity recorded during the evaluation sequences is analyzed to determine the amplitude and delay of event related potentials (ERP) produced during the events in the sequences. The ERPs are used to determine the understanding of the commercial by using product attributes as the stimuli, the value of the product by using price stimuli, the intent to buy the product by using purchasing stimuli and the memory of the product by using product stimuli.

These together with other objects and advantages which will be subsequently apparent, reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

FIG. 16 depicts the understanding test event sequence;

FIGS. 17 and 18 illustrate equipment setups for creating the video tape shown to the subject;

FIG. 24 illustrates the analysis sequence for brain wave signals.

DESCRIPTION OF THE PREFERRED EMBODIMENTS

Figure 1:
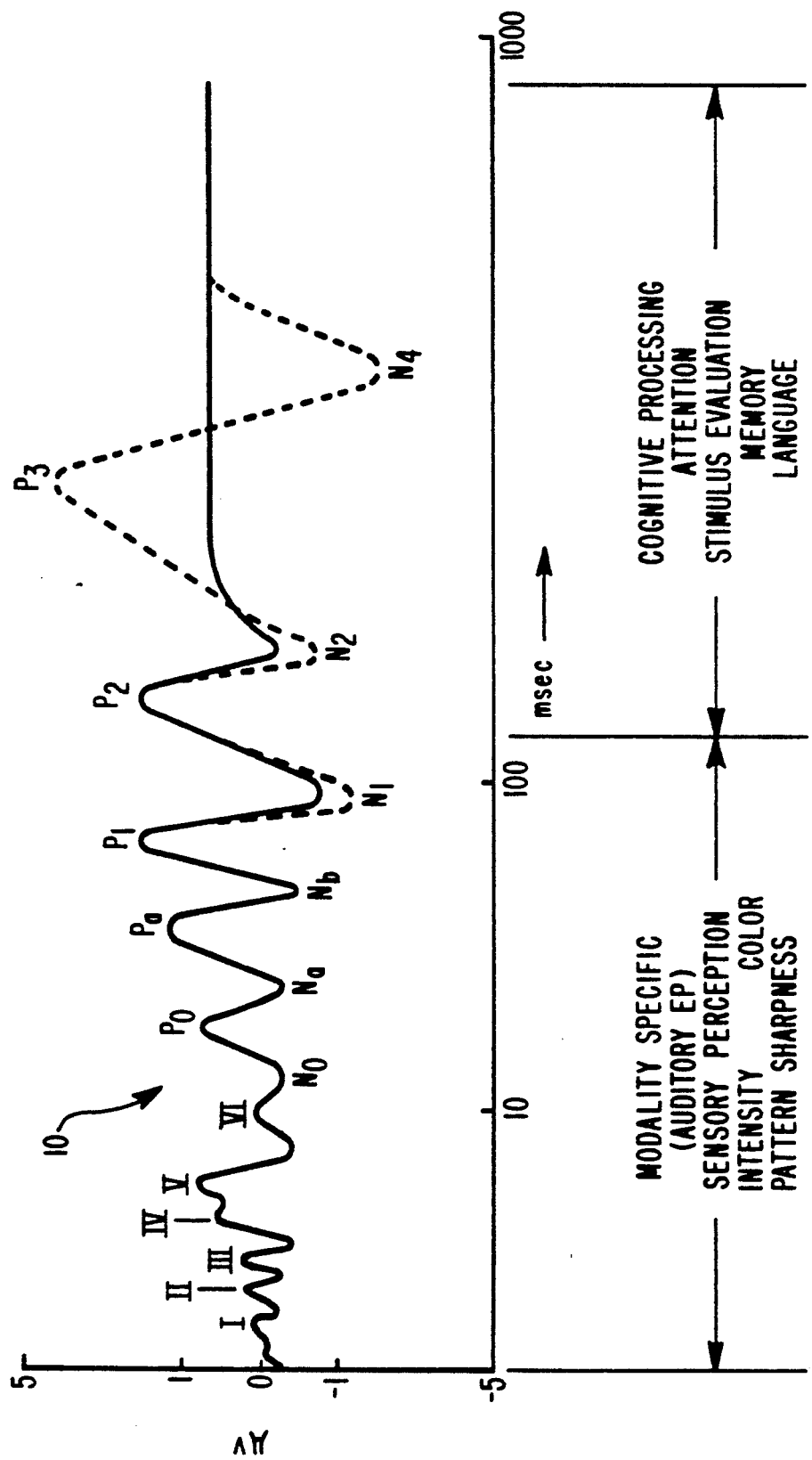
FIG. 1 is a plot of a typical event related potential (ERP)

This invention is directed to analysis and interpretation of cortical electrophysiological activity and particularly to recording and analysis of a subject's electroencephalogram (EEG) during a commercial, and recording and analysis of event related potentials (ERP) in evaluation sessions subsequent to the commercial. The recorded EEG is a continuous recording of electrical activity of the subject's brain during the commercial. An ERP is the electrical activity of the brain which is evoked by some environmental stimulus such as the presentation of a word or picture on a movie screen. An ERP is recorded for each evoking event, the same or similar events are presented a number of times and each ERP to each presentation is summed and averaged to improve the signal to noise ratio. FIG. 1 illustrates a typical ERP waveform 10 with the peak designations commonly used by those of skill in the art for the different waveform peaks therein and the types of mental activity that are signified by the peaks. The ERP reflects both primary sensory processing (modality specific) and cognitive processing depending on the tasks and the subject's interpretation of the stimuli. ERP measures are objective in that they do not require a behavioral response by the subject and for this reason have a significant advantage over subjective interview paper and pencil methods. ERP measures also enable specific features of the commercial to be evaluated and measured. EEG techniques provide general non-directed measures of overall arousal and cognitive processing. The combination of EEG and ERP can measure an indication of the specificity of the EEG response to the commercial. This invention provides an apparatus and a method for objectively measuring the effect of television advertisements and other short films using a physiological approach that can measure the specific impact of the film.

This invention includes recording the EEG during a commercial or short film and measuring specific frequencies of the EEG produced during the short segments of the commercial. The amplitude of the frequencies measured represents general attention and cognitive processing. After the commercial is viewed ERPs are recorded during a number of different tasks and the amplitude and or latency of the response is determined. The result is the measurement of the subject's memory or awareness of the contents of the commercial, understanding of the commercial and the advertised product, an indication of a subject's commitment to buy the product advertised which is a measure of persuasiveness of the message and an indication of the perceived value placed on the product by the subject. To obtain a representative sampling at least 20 subjects should be tested.

EEG activity recorded from different locations is sensitive to specific types of tasks in which the subject is engaged. Verbal and emotional tasks have an effect on overall EEG activity recorded from over the left cerebral hemisphere while spatial tasks alter EEG activity recorded from over the right cerebral hemisphere. Specific frequencies of the EEG, for example activity between 8 and 12 hertz (alpha activity) and activity between 16 and 24 hertz (beta activity), are sensitive to specific cognitive activity. Alpha activity measures intake or rejection of environmental stimuli and reflects attention to the commercial and beta activity measures both emotional processing and cognitive demand.

To determine attention to the commercial and cognition generated by the commercial, the EEG is recorded and analyzed for alpha and beta activity while a person watches the television advertisement. A thirty second advertisement is presented and the subject is instructed to watch the advertisement as he would watch an advertisement at home. During EEG analysis, the EEG is divided into time segments and the magnitude of alpha and beta activity is measured during each segment. The segments are preferably less than four seconds long and preferably around one second long. One second is about as short as is practical because the digitization rate must be twice as fast as the highest frequency and preferably 3 to 4 times as fast. The analyzed segments can be concatenated throughout the film or only important segments can be analyzed.

Figure 2:
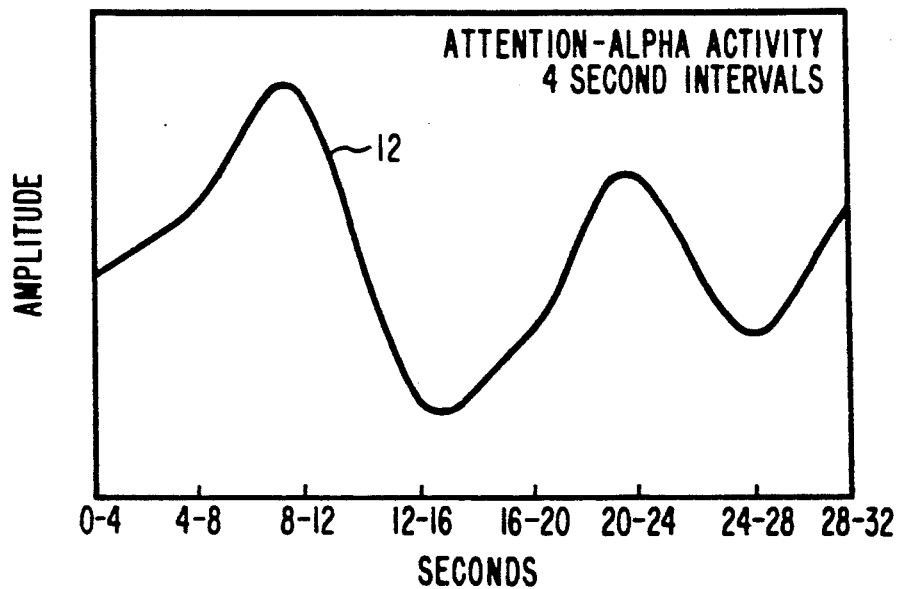
FIG. 2 is a graph of attention levels during a commercial.
Figure 3:
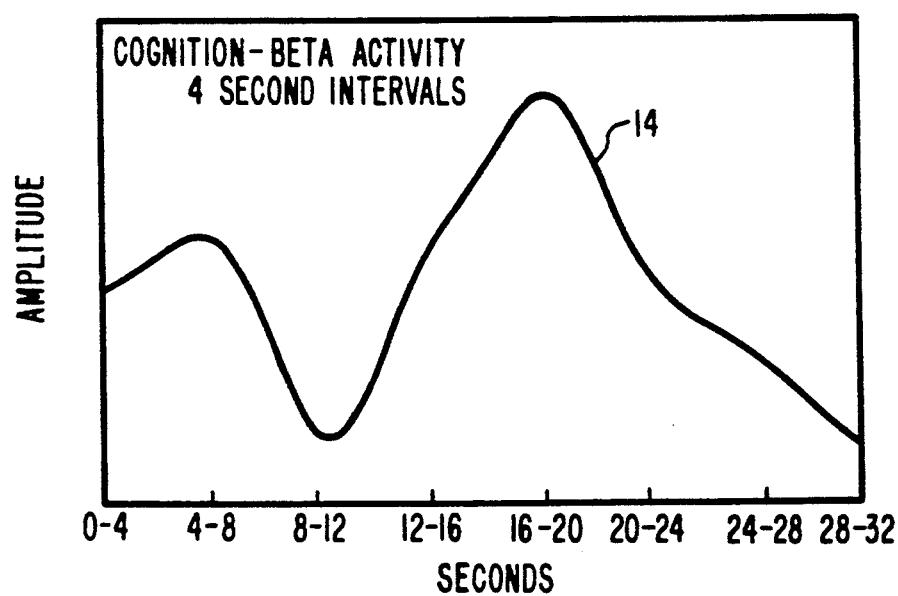
FIG. 3 is a graph of cognition activity during the commercial of FIG. 2.
Figure 4:
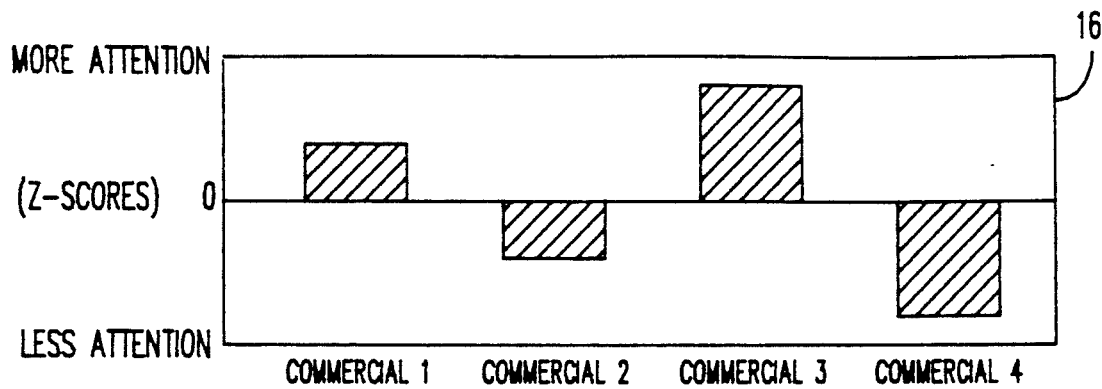
FIG. 4 is a bar chart comparing attention levels of several commercials.
Figure 5:
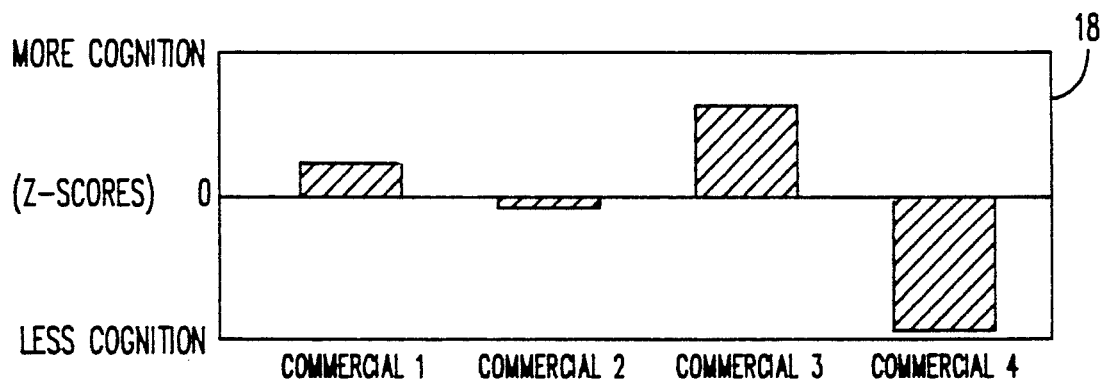
FIG. 5 is a bar graph comparing cognition levels of several commercials.

When the magnitude or amplitude of the alpha and beta portions of the frequency spectrum of the EEG segments are plotted the subject's attention and cognition during the commercial is provided as illustrated in FIGS. 2 and 3. By providing the determined magnitude values of FIGS. 2 and 3 after testing as the commercial is being shown to the producer, the effectiveness of the intended attention getting segments of the commercial can be determined along with the cognition by the subject during the commercial segments. The commercial producer can then fine tune the segments of the commercial designed to get the attention of the subject as well as the segments designed to make the subject think about the message being conveyed by the commercial. By determining the average attention levels and cognition levels for a series of commercials for a particular product the attention levels and cognition levels of various commercials can be compared as illustrated in FIGS. 4 and 5 using the following formula:

$$\text{Z-Score} = (\text{Score} - \text{Sample Mean})/\text{Standard Deviation} \quad (1)$$

, where the Score is the value of interest and the Sample Mean is average value of all related measurements taken over the entire value of interest sample set. This formula transforms the data from different commercials to a standard or common scale so that advertisements can be compared to each other. Bar graphs such as those illustrated in FIGS. 4 and 5 will allow a producer or advertiser to determine which commercial for the product is likely to be the most successful at getting the subject to pay attention to and think about the advertisement.

Late components of the ERP, particularly late positive components (LPC) and late negative components (LNC) are related to a number of memory processes involved with both initial encoding and subsequent recognition and recall performance as illustrated in FIG. 1. An LPC is a positive peak in the ERP that can occur with a latency varying from 250–750 milliseconds after the presentation of a stimulus. The peaks are traditionally denoted for example as P3 (see FIG. 1), where P indicates positive and 3 indicates the third positive peak in the sequence or P followed by the latency measured in milliseconds at which the peak occurred, for example P300. Isolated words presented within a list of words are recalled better only if they also generate a large P3 during initial presentation. ERPs recorded during the encoding of words that involve a semantic congruity judgment are related to the performance on a future recognition test. A larger late positive component (P3 or P300) is recorded from words that are subsequently recognized than words that are not recognized. Late positive components are larger for correctly identified items on a recognition test. The amplitude of a positive component at 400 milliseconds (P4 or P400) is larger to recognized photographs of persons, paintings, objects and places. Words correctly recognized as having been seen during an earlier task are associated with a larger P650. Late negative components around N400 and the actual latency of the component is associated with cognition about the event presented.

When assessing the impact of advertising several questions arise: One, will the product advertised be remembered in the future; two, how well is the product remembered at some specific time in the future; three, is the subject to buy the product in the future; four, what would the person pay for the product; and five, does the subject understand what the advertisement is trying to convey.

Figure 6:
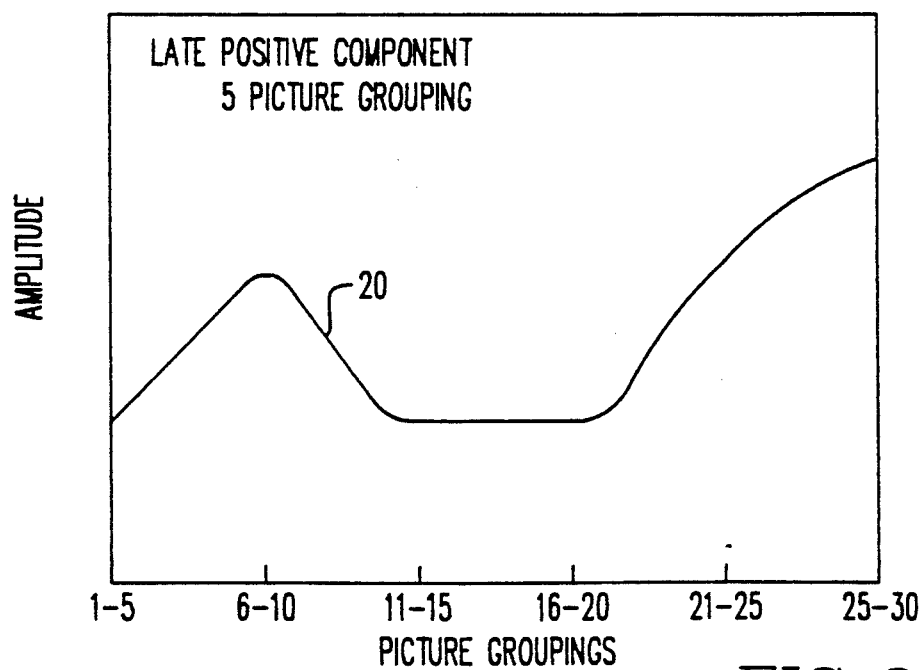
FIGS. 6 is a graph of the memorability of a commercial.
Figure 7:
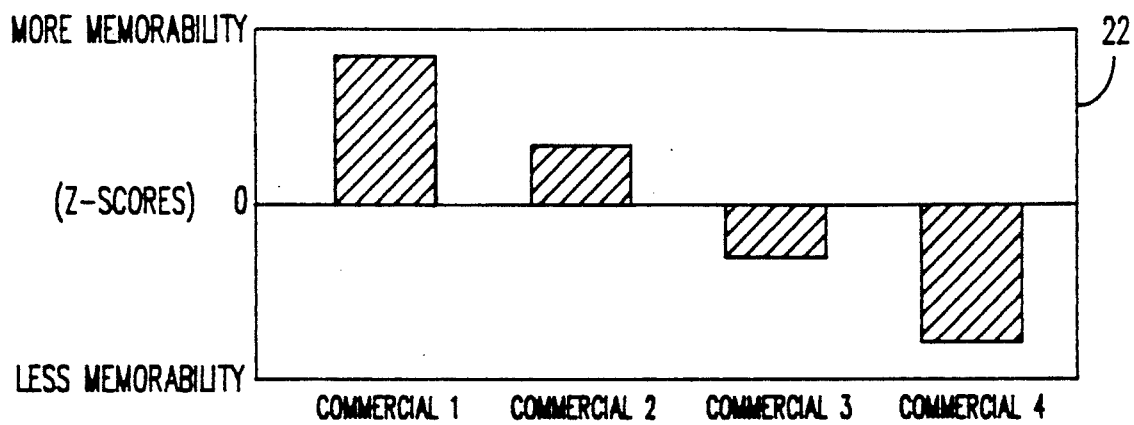
FIG. 7 is a bar chart which compares memorability of several commercials.

To determine how well the commercial will be remembered the commercial is re-presented to the subject as brief pictures of the commercial each shown for 150 milliseconds in their correct sequence. The brief pictures can be taken from the commercial in increments of one second apart for a thirty second commercial or as little as ¾ seconds apart to provide a more continuous review of the commercial. The amplitude of the late positive component (LPC) with a latency in the range of 350 to 600 milliseconds in the ERP for groups of adjacent pictures is determined and averaged to indicate which parts of the commercial are remembered best. FIG. 6 illustrates the memorability (awareness) for groups of five pictures when pictures are presented at one second increments for a thirty second commercial. This technique provides information on which parts of the commercial are remembered best. An overall memory score can be calculated for each commercial by averaging the grouped picture scores and the commercials can be compared for memorability using the averages scores as illustrated in FIG. 7. It is also possible, rather than presenting time-wise evenly spaced commercial frames, and possibly missing an important frame, to divide the commercial into segments that correspond to important parts of the commercial and to present frames related to those segments. In either situation a high late component amplitude indicates that a specific segment of the commercial or the overall commercial received a high level of attention and cognition and as a result should be remembered well.

Figure 8:
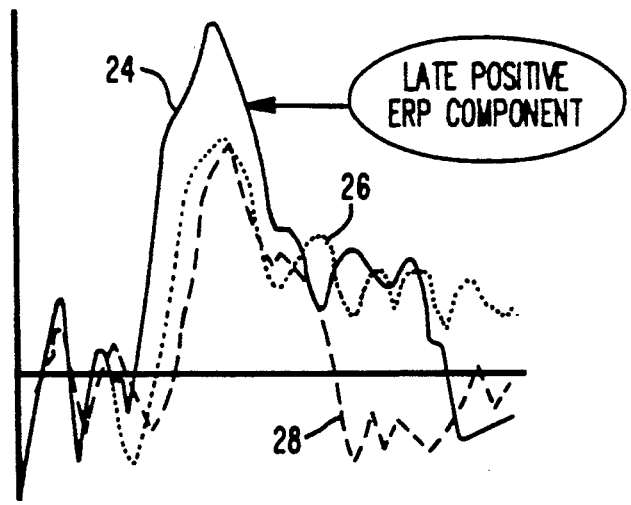
FIG. 8 is a graph indicating the memorability of a product several weeks after seeing a commercial.

To determine the memory of a commercial after a substantial delay, such as a 3.5 week delay after the commercial is presented, three types of pictures are shown to the subject: pictures from the advertisement containing the advertised product, pictures from the advertisement which do not contain the product and pictures from other advertisements and television shows. FIG. 8 illustrates the amplitudes of the late positive components with a latency in the 300 to 500 millisecond range for pictures of the product (solid line 24), for pictures from the advertisement that do not show the product (dotted line 26) and pictures from other advertisements and television programs (dashed line 28). If the late positive component amplitude for the product is higher than the late positive components for the other slides, as depicted in FIG. 8, the long term memorability of the product is good. If however, the late positive component amplitude of the product is lower than the late positive components of the other slides the long term memorability of the product is low. The long term memorability of various products can be compared by averaging the responses to the pictures showing each product and depicting the average response values using a bar chart similar to that illustrated in FIG. 7.

The evaluation of a subject's commitment to buy an advertised product and the subject's understanding of the content of the advertisement and features or attributes of the product advertised as well as the value (price) the subject places on the product involves the measurement of the semantic knowledge or meaning learned from the advertisement. Semantic knowledge represents our general factual and conceptual knowledge, beliefs and values concerning a specific area and which is acquired through experience, education, advertisement, media, etc. ERPs provide a very sensitive measure of the emotional impact of, the connotative meaning of, and the semantic association between words as well as the degree to which words are expected within a specific context. The semantic knowledge measure provided by an ERP is expressed by the enhancement of a late negative component with a latency of between 300 and 500 milliseconds.

Figure 9:
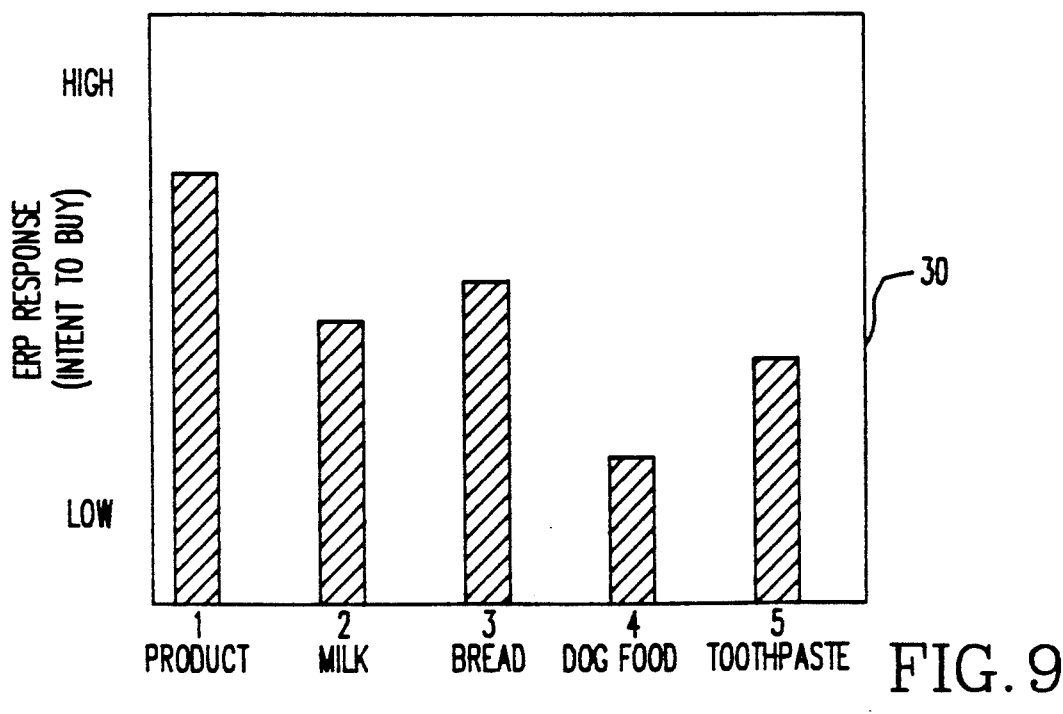
FIG. 9 is a comparison of intent to buy a product compared to reference products.

Semantic priming is used to determine the enhancement of a late negative component amplitude for tests related to intent to buy, understanding and value. In this procedure a list of words is presented to the subject and the degree of semantic association between the words in the list is varied. The typical behavioral result is that reaction time is faster and more positive to words which are preceded by words that are semantically associated along some dimension. For example, the enhancement of the late negative component amplitude will be greater for a sentence such as "He liked lemon and sugar in his tea" than for a sentence such as "He liked lemon and sugar in his coffee". That is the ERP varies as a function of how likely the subject thinks that a word would end a particular sentence. To measure the commitment to buy a product a sentence is presented such as "The next time I go to the supermarket I intend to buy" followed by one of the product words such as milk, fish or paper towels or pictures of these products. One of these products is the product advertised and one is a reference product. Since the ERP is a function of how well the word or picture completes the sentence for the subject, the ERP is able to distinguish between those products that have a high likelihood of being bought the next time the person goes to the store and those products that have a low chance of being bought. In this way, the likelihood that an advertised product will be bought as compared to products which are traditionally bought (reference products) when a person enters a store can be compared. A graph of the enhancement of the late negative component for a number of products to which the advertised product is compared is illustrated in FIG. 9. By using a product, such as milk or bread, which has a high historical incidence of purchase as a reference and testing alternative advertisements against the reference, the advertisement that best increases the subject's commitment to buy the product can be identified and compared using a graph similar to that illustrated in FIG. 7.

Figure 10:
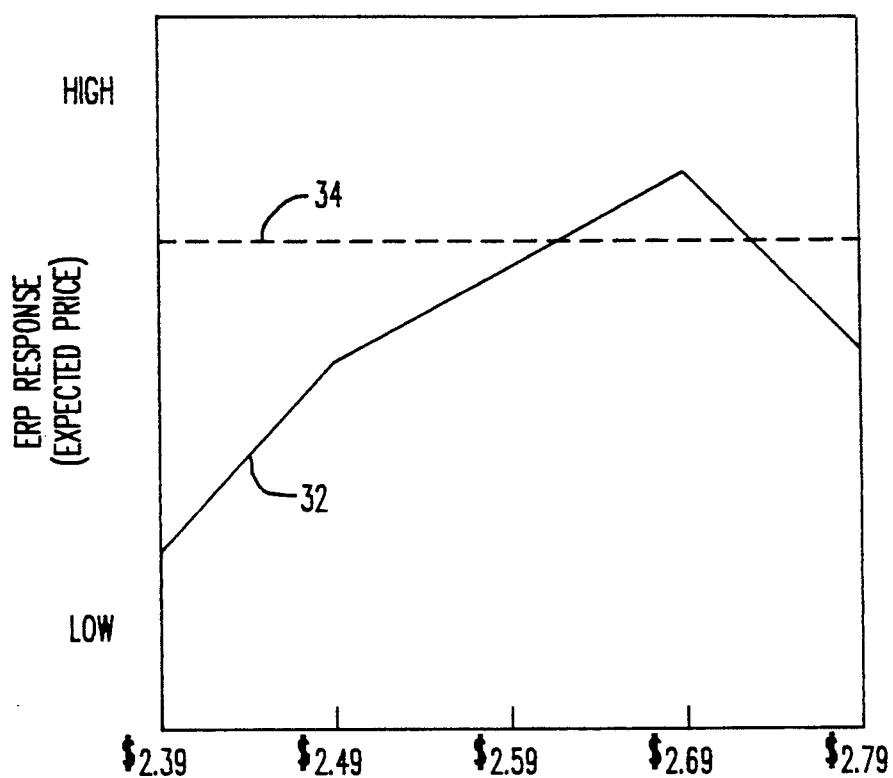
FIG. 10 is a graph of ERP response versus product value.

Determining the value (price) of a product can be accomplished in much the same way as the intent to buy by looking at the value of the latency of the late negative component in the 300 to 700 millisecond range. The later the response the closer the value is to the subject's perception of the value. The subject is presented with a sentence such as "When purchasing (a product) I would pay" followed by a price. The product picture can be presented with the sentence. Sentences which use the advertised product as well as various products such as milk, bread and dog food can also be presented with varying prices as reference products. The actual prices for the non-advertised products in the region in which the test is being conducted should be included in the prices presented, so that reference ERP response values can be determined. FIG. 10 illustrates the latency of the ERP responses for prices of an advertised product with a price of $2.69 being the most expected. The dashed line in FIG. 10 indicates the average latency to a reference product, such as milk, when the actual local price is presented.

Understanding of the product is divided into an ad profile and a product profile. The ad profile measures the understanding of the tone of the advertisement, and the product profile is an indication of the understanding of the characteristics of the product advertised.

Figure 11:
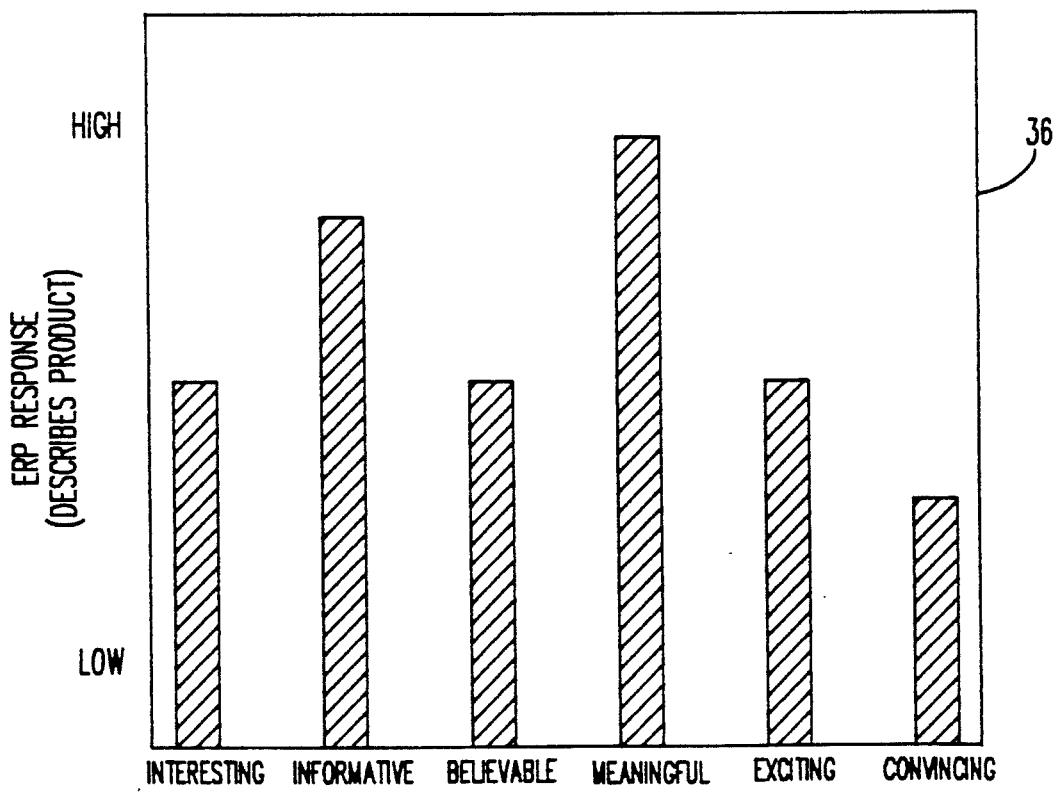
FIG. 11 is a graph showing the understanding of the advertisement.

The ad profile is measured with a procedure that is similar to measuring intent to buy and value. A sentence is presented such as "I believe the first commercial was" and next words are presented such as "interesting, informative, believable, meaningful, exciting, and convincing". The product profile focuses on determining the amplitude of the late negative component around N400. The enhancement of the ERP (increase in the positive change in the amplitude) to each word is recorded and analyzed to determine which words best characterize the advertisement and a graph is presented as illustrated in FIG. 11.

Figure 12:
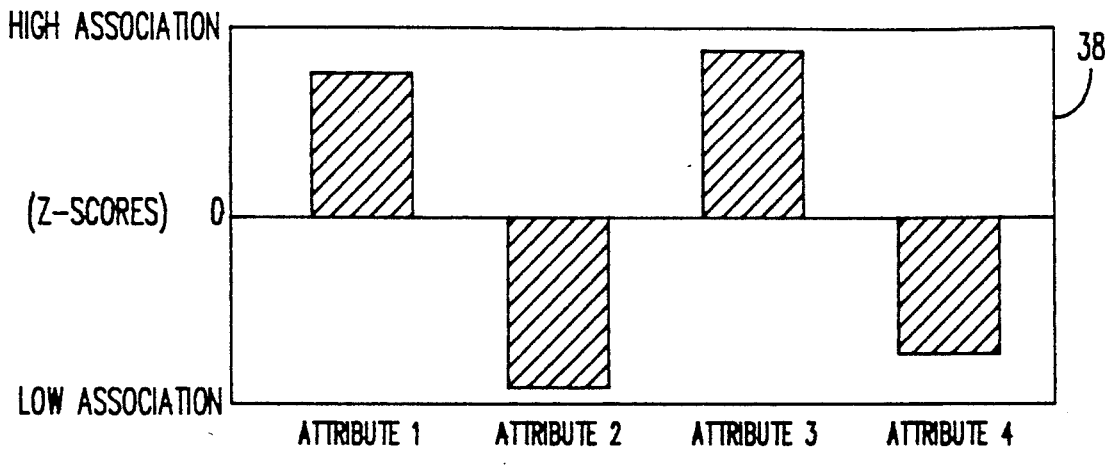
FIG. 12 is a bar chart of product attribute profiles for four different advertisements for the same product with the values averaged.

The product profile is also determined by using the priming method. A picture of the product is presented followed by a descriptive attribute or characteristic of the product. For example if a picture of a diet cola soda is presented, the ERP amplitude will vary depending on how strongly the subject associates the product with the attribute "low calorie" or with the attribute "good tasting." The attributes presented should reflect not only the desired message of the commercial but other messages of less relevance or of no relevance. The magnitude of the ERP can be plotted using a graph similar to FIG. 11 where the attributes are indicated across the bottom. It is also possible to combine attribute values for several different advertisements and produce a product attribute bar chart as illustrated in FIG. 12 which illustrates the combination of product profiles from four advertisements such as when a product such as tomato juice is advertised.

From the ad profile and the product profile the advertiser can determine whether the message originally intended by the advertisement is being communicated to the subject, thereby allowing the advertiser to fine tune the advertisement for a particular message.

Figure 13:
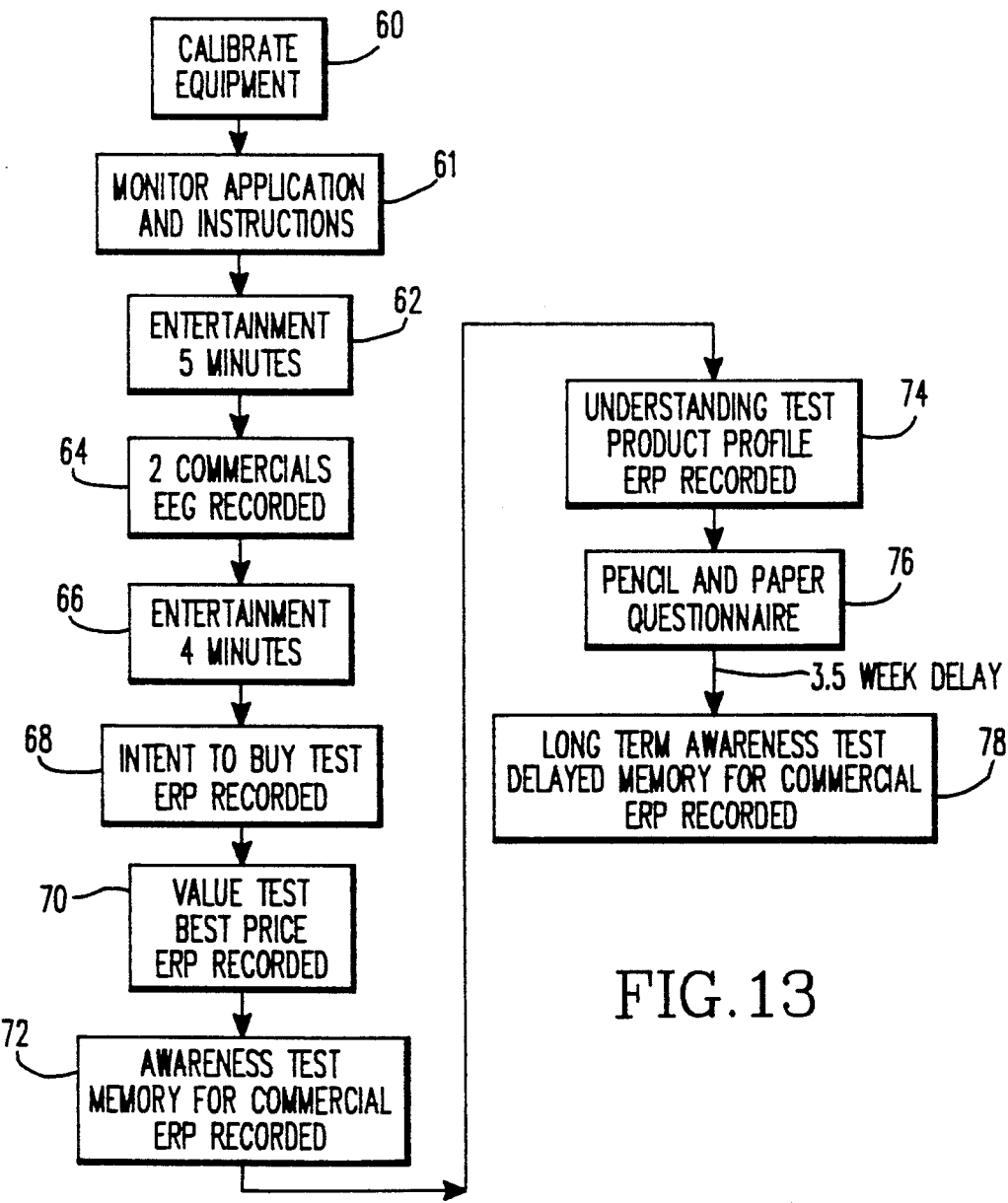
FIG. 13 illustrates the test site sequence used to test a commercial.
Figure 14:
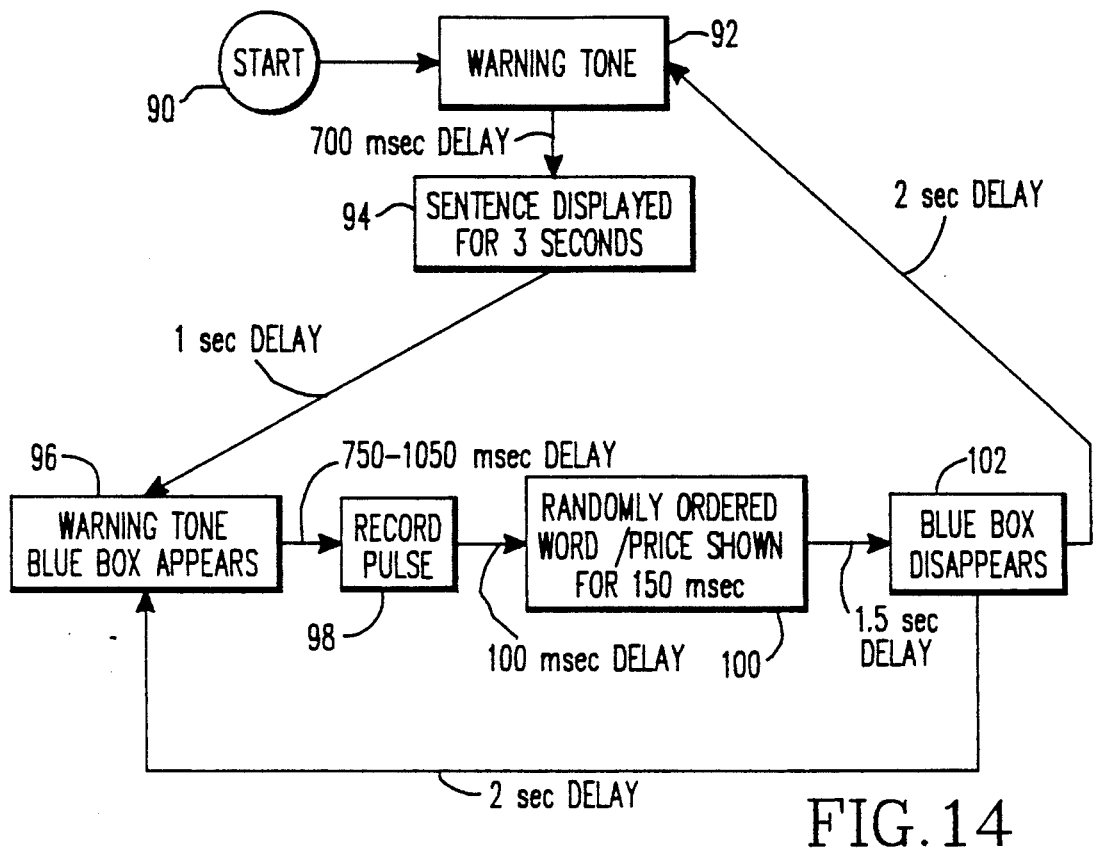
FIG. 14 shows the event sequence during the intent to buy and value tests.
Figure 15:
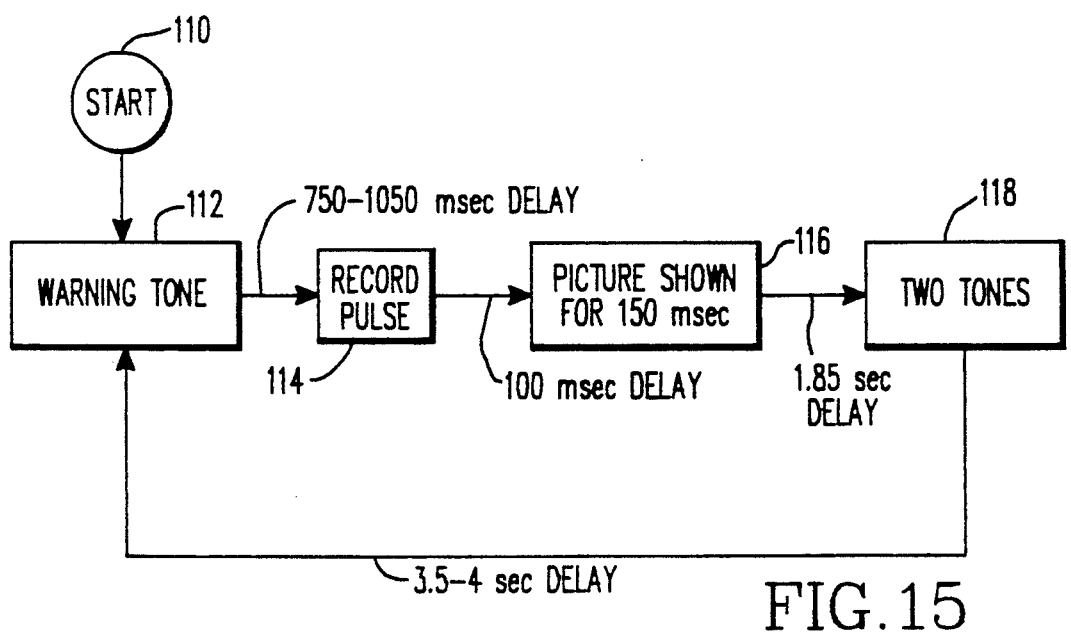
FIG. 15 illustrates the event sequence for the memory awareness tests.

The procedure used to test a commercial attempts to create an environment very similar to that which would be found in a person's home while they are watching TV. The subjects are preferably tested in groups of two and each subject is seated in a comfortable chair in a market research test facility where external disturbances can be minimized. The procedure followed is illustrated in FIG. 13. First the equipment used to record the EEG is calibrated 60 followed by a brief description of the procedure and attachment 61 of the monitor electrodes to the subject. Once the subjects are relaxed, a videotape player is started which shows 62 entertainment for five minutes followed by two commercials 64 during which the EEG is recorded. One commercial is a reference commercial and the other commercial is the commercial for the product being advertised. Following the commercials four minutes of entertainment are presented 66. After the entertainment the intent to buy test is conducted 68 during which the electrical activity is recorded for ERP analysis. The timing sequence of images during this test is illustrated in FIG. 14. Following the intent to buy test is the value test 70 during which the electrical activity for ERP analysis is also recorded followed by the awareness test 72 and the understanding test 74 during both of which the brain wave activity is recorded for ERP analysis. The value test timing sequence of prices is also illustrated in FIG. 14, the awareness test image timing sequence is illustrated in FIG. 15 and the understanding test timing sequence for presented words is illustrated in FIG. 16. The sequence of events 62-74 are recorded on a single continuous videotape which is presented to the subjects without interruption. After the tests are completed and the monitors are removed from the subjects, the subjects are asked to complete a paper and pencil questionnaire 76 during which the subjective impressions of the subjects are measured for comparison with the objective information gathered. Approximately three and one-half weeks after the original commercial and test session, the long term awareness test 78 can be conducted during which the long term memory of the commercial is tested. The timing for this procedure is also illustrated in FIG. 15. The sequence of tests illustrated in FIG. 13 is not fixed and can occur in any order and some of the tests can be omitted if desired by the advertiser.

FIG. 14 illustrates the sequence of images and signals produced by the videotape during the intent to buy and value tests. After this segment of the tape starts 90, a warning tone is provided 92 to the user. 700 milliseconds later the sentence is displayed 94 for three seconds. One second after the sentence disappears a warning tone is provided to the subject and a blue box appears 96 on the television. Subsequent to the warning tone a record pulse is provided 98 to a computer to start recording the electrical brain wave activity of all subjects. 100 milliseconds after the record pulse and 850-1150 milliseconds, randomly selected, after the warning tone appears one of the randomly ordered words or prices is shown to the subject for 150 milliseconds. The random variation between the appearance of the blue box and the word reduces the contingent negative variation drift which occurs in the presence of regularly spaced stimuli. The 100 millisecond period after the record pulse is used to record activity which is later used as a base line measure during ERP analysis. 1.5 seconds after the word or price disappears the blue box disappears 102. If all the words or prices have not yet been displayed, a two second delay is provided after which the warning tone is sounded and the blue box again appears. If all the words or prices have been shown to the user the warning tone is produced 92 and another sentence is displayed 94. This cycle continues until all the words and- /or prices have been shown to the user in random order at least 5 to 15 times. The responses to the same words or prices for the plural repetitions are later combined by averaging during the analysis process, so that any unusual responses and random noise will be reduced in the response data.

The memory awareness test 72 and 78 is presented as illustrated in FIG. 15. After the segment starts 110, a warning tone is provided 112 to the subject after which a record pulse is transmitted 114 from the tape player to the computer system recording brain activity. 100 milliseconds after the record pulse and 850-1150 milliseconds, randomly chosen, after the warning tone the picture is shown 116 for 150 milliseconds. After the picture disappears from the television a 1.85 second delay is provided after which two tones are provided 118 to the subject. After a delay of 3.5 to 4 seconds, also randomly chosen, the warning tone again appears 112. This sequence continues until all pictures have been shown to the subject.

The understanding test, after it is started 130, also provides a warning tone and produces 132 a blue box on the television screen as illustrated in FIG. 16. After a random delay of between 850 and 1150 milliseconds, the first word sentence is shown 136 to the subject for 150 milliseconds. The variable word is a product such as milk or the product being advertised. Between the first word and the presentation 140 of the second or attribute word, for example "exciting", a record pulse is provided 138 to start the computer recording. The delay between the first word and the second word is randomly chosen Within the range of 500-700 milliseconds. Once again the record pulse occurs 100 milliseconds before the second word is shown 140. 1.5 seconds after the second word disappears from the screen the blue box disappears 142. After a two second delay the warning tone and blue box reappear 132 and this sequence continues until the attributes are presented for the number of times previously mentioned.

Throughout the above discussed tests the 1/L audio channel is used as the audio output for the subject and the 2/R audio channel is used as the trigger line for the record pulse to the computer system. The entertainment segments and the commercial are recorded directly from other VCR tapes using a standard video mixing set up. At the very beginning of each commercial the record pulse is recorded as a tone of for example 1000 Hz on channel 2/R. This can be accomplished using a tone generator connected to a video mixer. The tone generator can be a personal computer such as the Commodore Amiga executing a tone generation routine. This audio trigger for the record pulse is provided on the first frame of each commercial and 100 milliseconds before the word or image in all other test sequences.

The intent to buy, value and product profile tests are recorded using a set up as illustrated in FIG. 17. A personal computer 150 with a display 152, such as the Amiga computer mentioned above, is used to directly feed a studio quality video recorder 154 such as the Sony U-Matic Videocassette Recorder Model VO-5856. The computer generates the warning tones, the blue box, the random delay, the trigger pulse the sentence, and the stimulus word as previously discussed With respect to FIGS. 14–16 using a program as illustrated by the pseudo code algorithm of Appendix 1.

The sequence for constructing the memory awareness test occurs in two stages. In the first stage the pictures to be used during the test are transferred, as illustrated in FIG. 18, from one video recorder 152 to a second video recorder 156 using the freeze frame capabilities of the video recorder 152. To do this the commercial is sequenced forward until the desired picture is displayed and the freeze frame capability of the video recorder 152 is activated and then the second video recorder 156 records the selected picture for seven seconds. This can be accomplished automatically by controlling the video recorders using a computer if a predetermined sequence such as a picture every second is desired. Once the pictures are recorded on the second video recorder 156, the tape with the seven second pictures is placed in the first video recorder 152. Using a script as illustrated in Appendix 2 attached hereto, the Deluxe Video Software by Electronic Arts of San Mateo, Calif. for the Amiga computer is used to control the transfer of the picture through a Commodore Amiga Genlock device 158. The attached script generates the warning tone and trigger tone and controls picture presentation for one commercial and in sequence a single memory awareness test. This test sequence may be of segments taken from the commercial at 1/30 second intervals while the seven second presentation can be reduced to as little as two seconds. This device can be configured to transfer the video recorder signal by setting a mask therein to transparent or to block the video signal by setting the mask to black. The script provided in Appendix 2 will keep the screen recorded by video recorder 156 blank for the necessary amount of time, produce the warning tones, delays, trigger pulses and flash the pictures onto the screen for the required amount of time followed by blackening the screen again.

Figure 19:
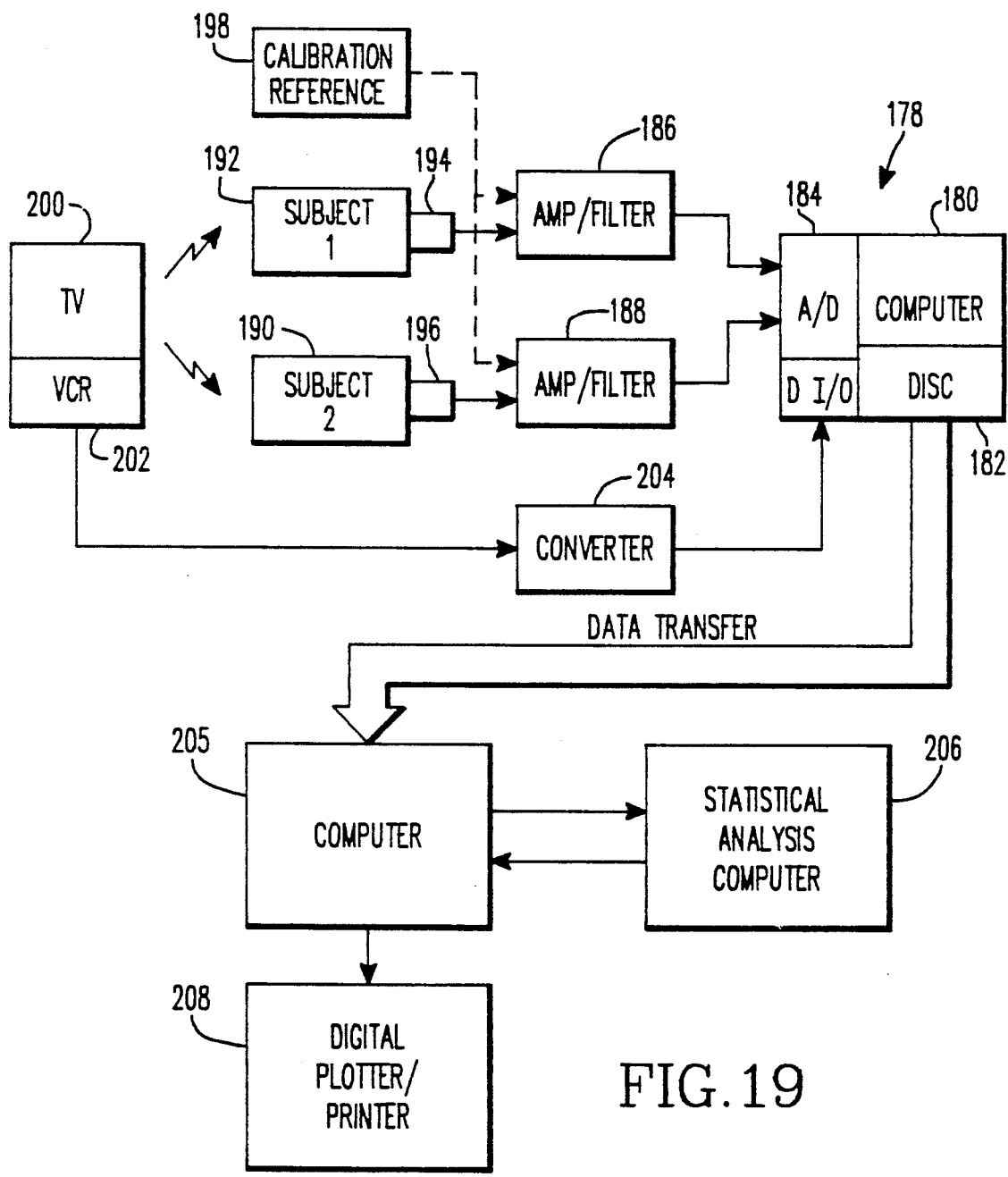
FIG. 19 illustrates the equipment used to perform the commercial analysis and testing.
Figure 20:
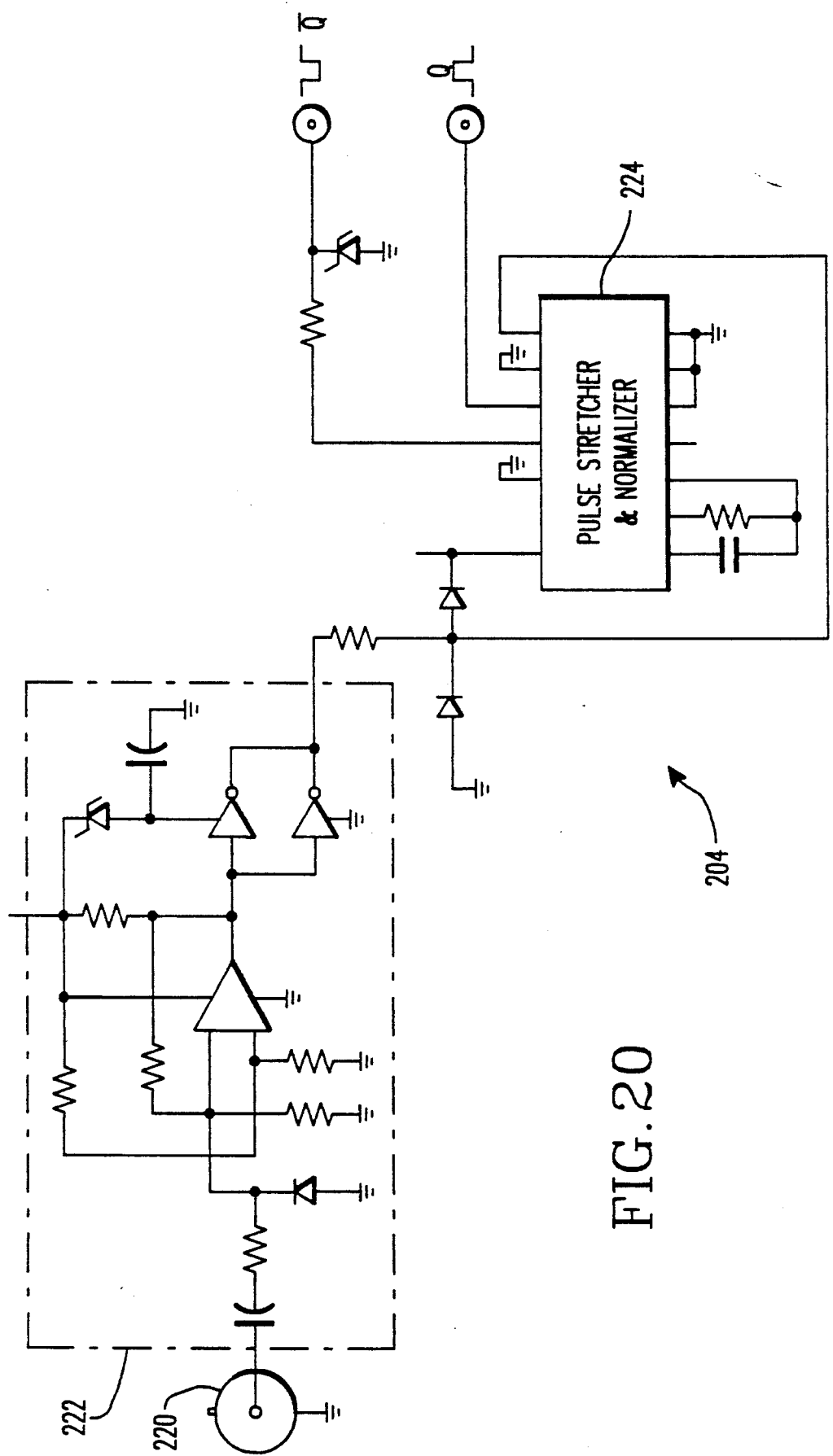
FIG. 20 is a diagram of the conversion circuit illustrated in FIG. 19.

During the data collection process, a conventional personal type computer 180, as illustrated in FIG. 19, such as an IBM AT with 3 megabytes of random access memory and a hard disk 182, is used to collect the brain wave data through a conventional 12 bit analog-to-digital converter 184 such as model 2801 from Data Translation sampling at 256 samples per second for each subject. The analog-to-digital converter 184 is multiplexed to sample the analog signals produced by amplifier/filtering circuits 186 and 187 corresponding to the subjects 190 and 192. The amplifier/filtering units 186 and 188 are preferably Grass Model 12 A5 Neuro Data Acquisition Systems available from Grass Instruments of Quincy, Mass. The EEG signals are provided to the units 186 and 188 by non-polarizing electrode sets 194 and 196. A suitable electrode can also be obtained from Grass Instruments. To calibrate the system a calibration reference 198 such as the Grass RPS 107 regulated power supply is connectable to the units 186 and 188. As the subjects view the television 200, which is preferably a conventional television similar to the one the subjects use at home, the VCR 202 providing the image signal also produces the record trigger tone which is applied to a converter 204 the details of which are illustrated in FIG. 20. The converter 204 applies a record pulse to a conventional digital input/output port which is part of the A/D converter unit 184. The computer 180 waits for the record pulse either in a conventional interrupt or polling fashion. After the data is collected and stored on the disk 182, it is transferred to a larger computer 205 which is capable of high speed digital analysis. A suitable computer 205 is the Masscomp 5600 available from Massachusetts Corp, Westford, Mass. The data transfer can be accomplished over various types of telecommunication networks or by storing the data on a floppy disk and transferring the data disk by mail. If the commercial testing and analysis is to be carried out contemporaneously with the commercial editing process, a telecommunications data transfer process is preferred. If however the testing and evaluation need not be expedited, the less costly postal service transfer method is preferred. The computer 205 can be coupled to a statistical analysis computer 206 which can be any general purpose computer such as a Mackintosh personal computer or IBM AT executing a standard statistical analysis package. The statistical analysis which compares different types of signal filtering will be discussed in more detail hereinafter. Once the computer 205 has performed the necessary analysis computations, the selected results are output using a digital plotter and printer 208. The distributed equipment arrangement illustrated in FIG. 19 could of course be included in a single portable unit rather than divided into two spatially separated units, so that analysis could be on the testing site and possibly contemporaneous with commercial production and editing.

The output of the 2/R channel of the VCR 202 is applied to an input 220 of a conversion unit 204 as illustrated in FIG. 20. The conversion unit 204 includes a converter 222 which converts the sine wave signal into a square wave signal. This signal is applied to a pulse stretcher/normalizer 224 available from Texas instruments as chip CD 4047 which outputs a digital trigger to the computer system 178. The positioning of this pulse on the tape needs to be within plus or minus one millisecond of the correct position. Based on this trigger pulse the computer system begins digitizing and digitizes for a predetermined length of time as determined by the control program for each test being performed. Instead of having predetermined recording time lengths, it is possible to place an end of recording pulse or pulses on the tape. These would be digitized in the same way. It is also possible for each recording stage to be controlled by a different number of pulses.

In the discussion below flowcharts for several programs are discussed in detail. The routines represented by the flowcharts are preferably implemented in the C programming language but other languages can be used depending on the computer being used.

As previously mentioned, before the commercials are viewed by the subjects the calibration reference 198 provides a calibration pulse through the amplifier units 186 and 188 for each subject. The amplifiers 186 and 188 are calibrated using a ten microvolt signal and the averaged digitized amplitude of this signal is stored as an ASCII character followed by a carriage return character at the beginning of each data file for each subject. The calibration routine, illustrated in FIG. 21, starts by initializing 240 variables such as initializing the digitized calibration pulse for each subject to zero. The computer 180 then loops on a decision block 242 waiting for a trigger indicating that the calibration reference is being applied to a particular amplifier. When the trigger occurs the value provided by the amplifier is digitized 244 followed by incrementing 246 a counter for counting calibration pulses. When thirty calibration pulses have been digitized 248, the thirty pulses are averaged 250 and stored 252 as previously discussed.

Figure 21:
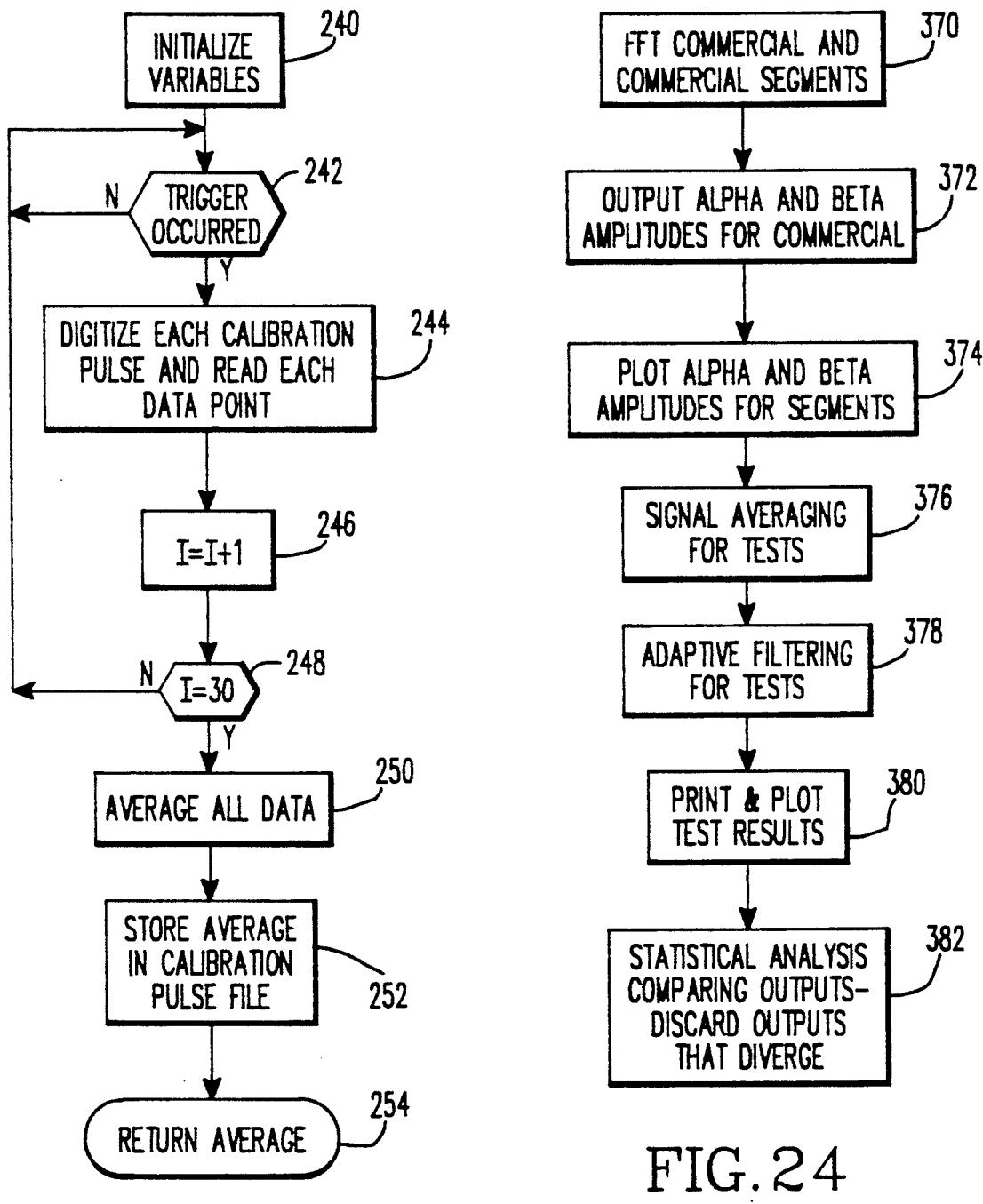
FIG. 21 is a calibrate routine flowchart.
Figure 22:
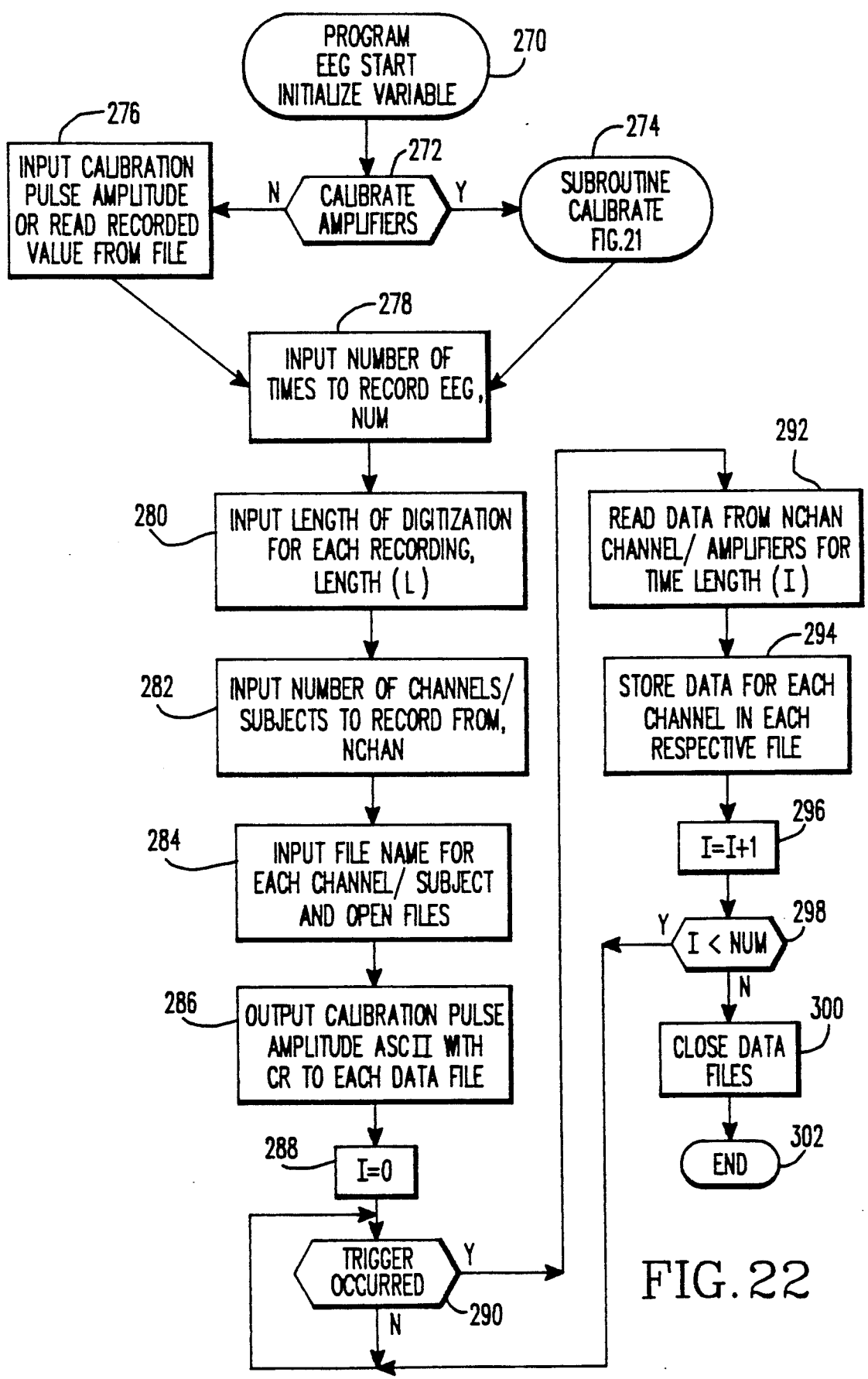
FIG. 22 is a flowchart of EEG digitization.

As illustrated in FIG. 13, two types of brain wave digitization occur, one for recording the EEG and one for recording the ERPs. The operation of the EEG digitization program is illustrated in FIG. 22. After this program has started 270, during which the variables are initialized, a determination is made 272 concerning whether to calibrate the amplifiers. If so the calibration routine of FIG. 21 is executed 274. If not the test instructor is allowed to input 276 calibration pulse amplitudes. The instructor then inputs 278 the number of EEG segments, the length 280 of each recording, the number of subjects 282 and the file name 284 for each subject. The program then stores 286 the calibration pulse amplitude at the head of each file. Next the segment counter I is set 288 to zero and the process enters a loop 290 waiting for the trigger pulse at the beginning of the commercial. After the trigger pulse is received the data from each channel is recorded 292 and stored 294 for each segment after which the segment counter is incremented 296. If the segment counter is less than the number of segments, the loop is traversed again. Otherwise the data files for the EEG are closed 300.

Figure 23A:
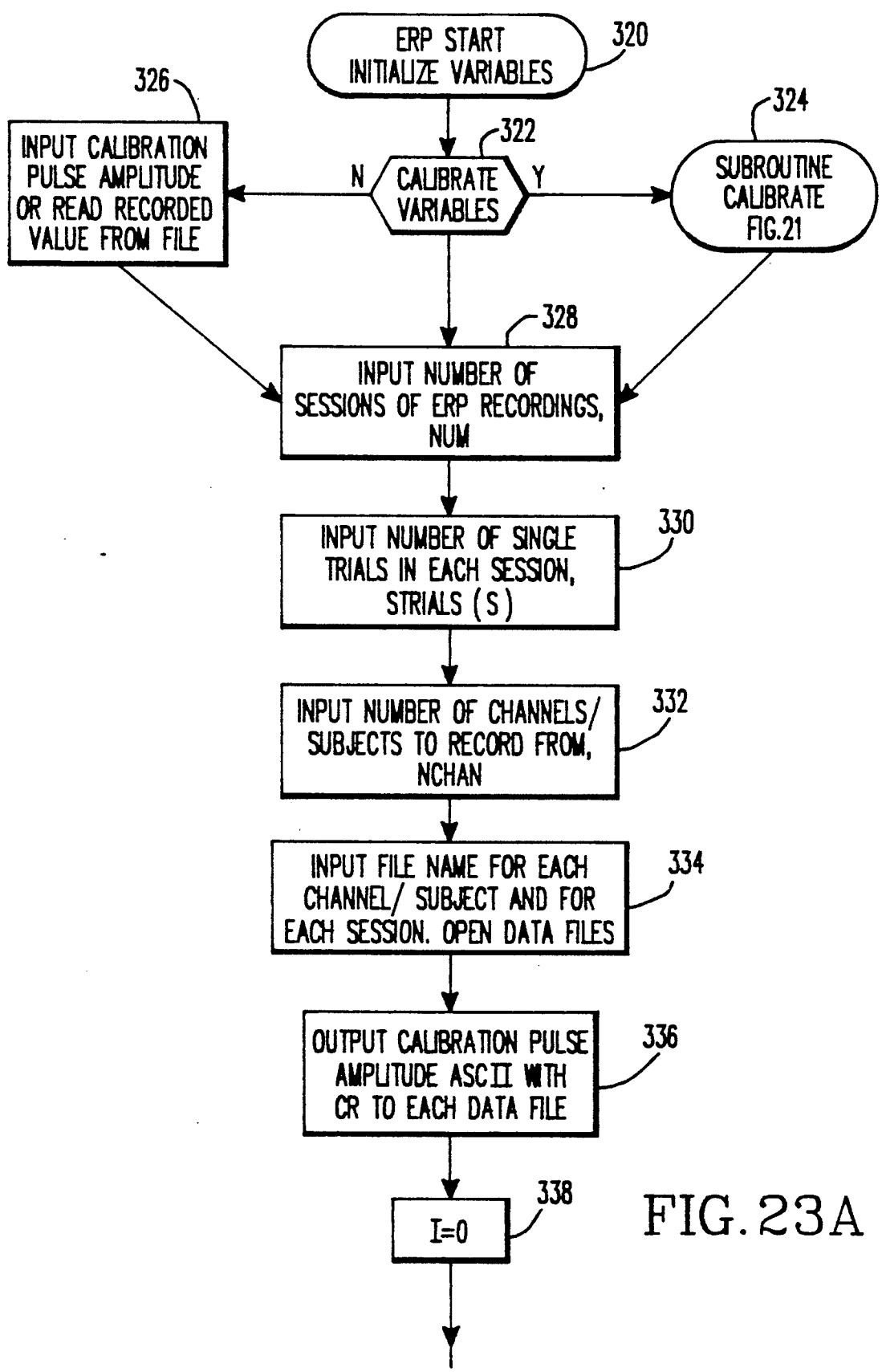
FIGS. 23A and 23B depict the program for ERP digitization.
Figure 23B:
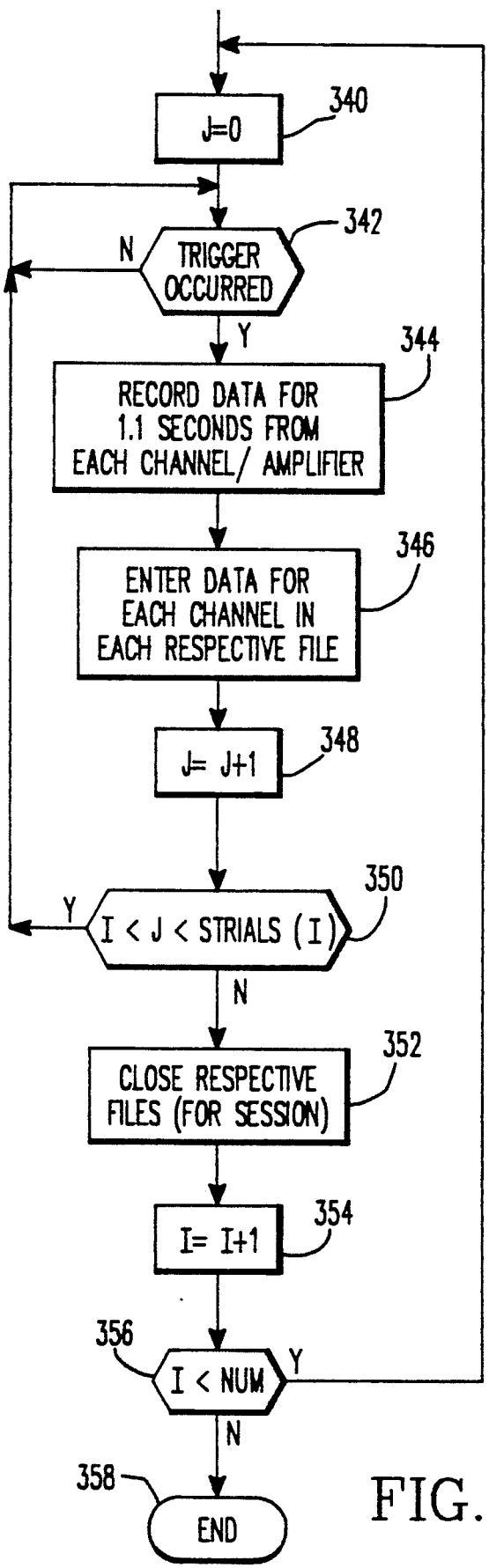

The ERP digitization program of FIGS. 23A and 23B starts 320 by initializing the various variables and thus allows the instructor to determine 322 whether calibration should occur, followed by executing the calibration subroutine or inputting 326 calibration pulse values. Once again the number of ERP sessions to be recorded is entered, followed by entering 330 the number of trials of each word or picture and entering 332 the number of subjects being analyzed. After the file name for each subject is entered 334, the respective calibration pulse amplitude is stored at the head of each file. Next the sessions pointer is initialized 338 to zero and the number of trials pointer is initialized 340. The process then waits 342 for the trigger pulse after which the data is recorded 344 and stored 346 for the trial. The trial pointer is then incremented 348, followed by a comparison 350 of the trial pointer with the number of trials entered. If all trials have not been done the process loops back to continue digitizing. If the trials have been done the respective session files are closed 352 followed by incrementing 354 the session pointer and a comparison 356 with the session number previously entered. If additional sessions are necessary the process loops back and performs those sessions.

The processes illustrated in FIGS. 22 and 23 allow the operator to enter the number of sessions and subjects at the beginning of each test thereby allowing the instructor to change these values as needed for different situations. This method of entering the variable data before each test requires that the tape player 202 be stopped after events 66-72 of FIG. 13, so that the instructor can enter the data. An alternative is to put all variable information in blocks of the flowcharts in FIGS. 22 and 23 at the beginning of the program and concentrate the remainder of FIGS. 22 and 23 into a single program. This would provide the advantage of not having to stop the recorder after each test and would allow the disturbing influence of the instructor to be removed from the room once the activity of block 62 in FIG. 13 has started. As another alternative it is possible to store the variable data in a fixed data file which is accessed during a test. In such a situation those portions of the flowchart which allow the entry of the data would be substituted with read instructions.

Figure 25:
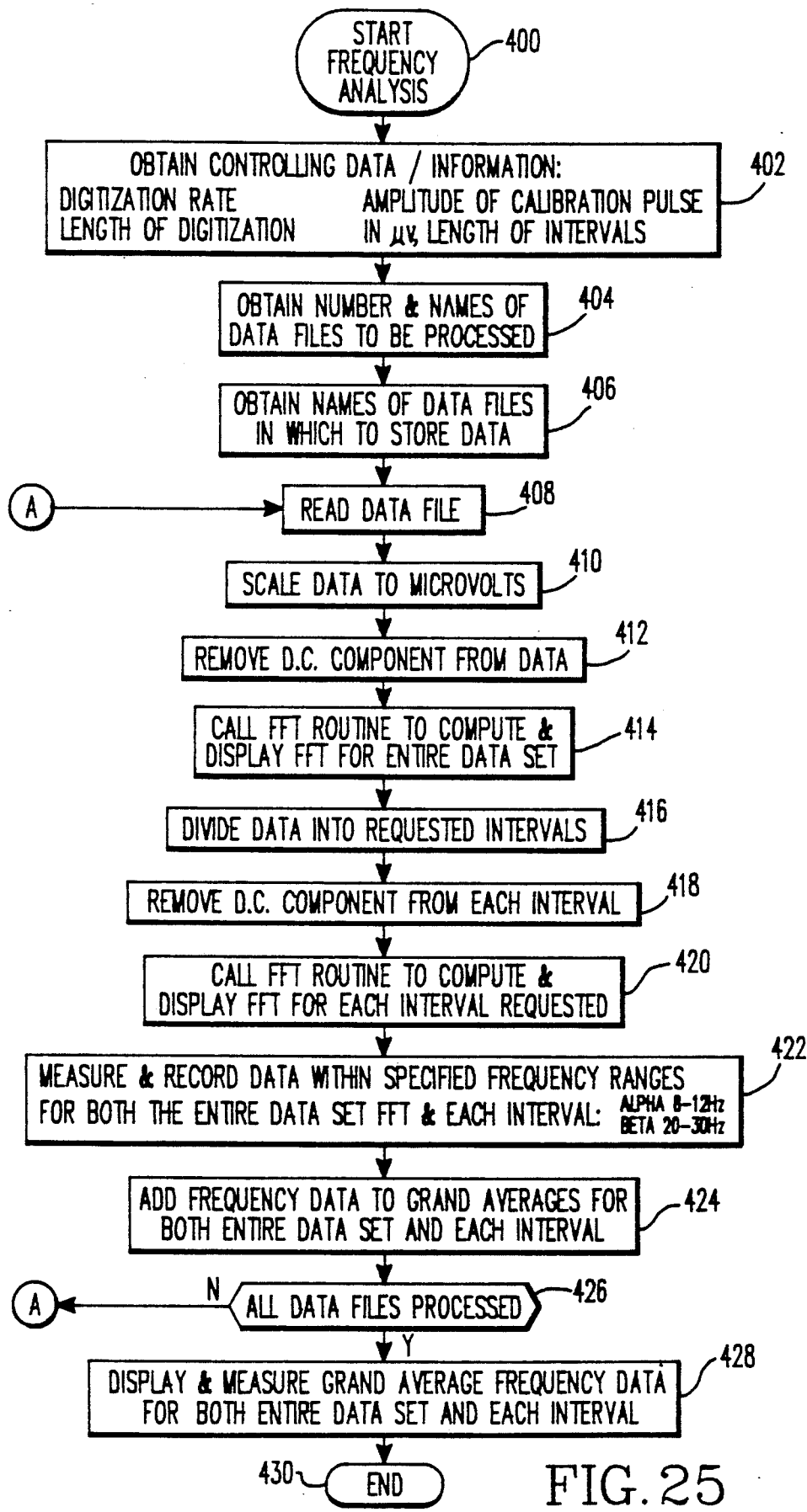
FIG. 25 depicts EEG frequency analysis.
Figure 26A:
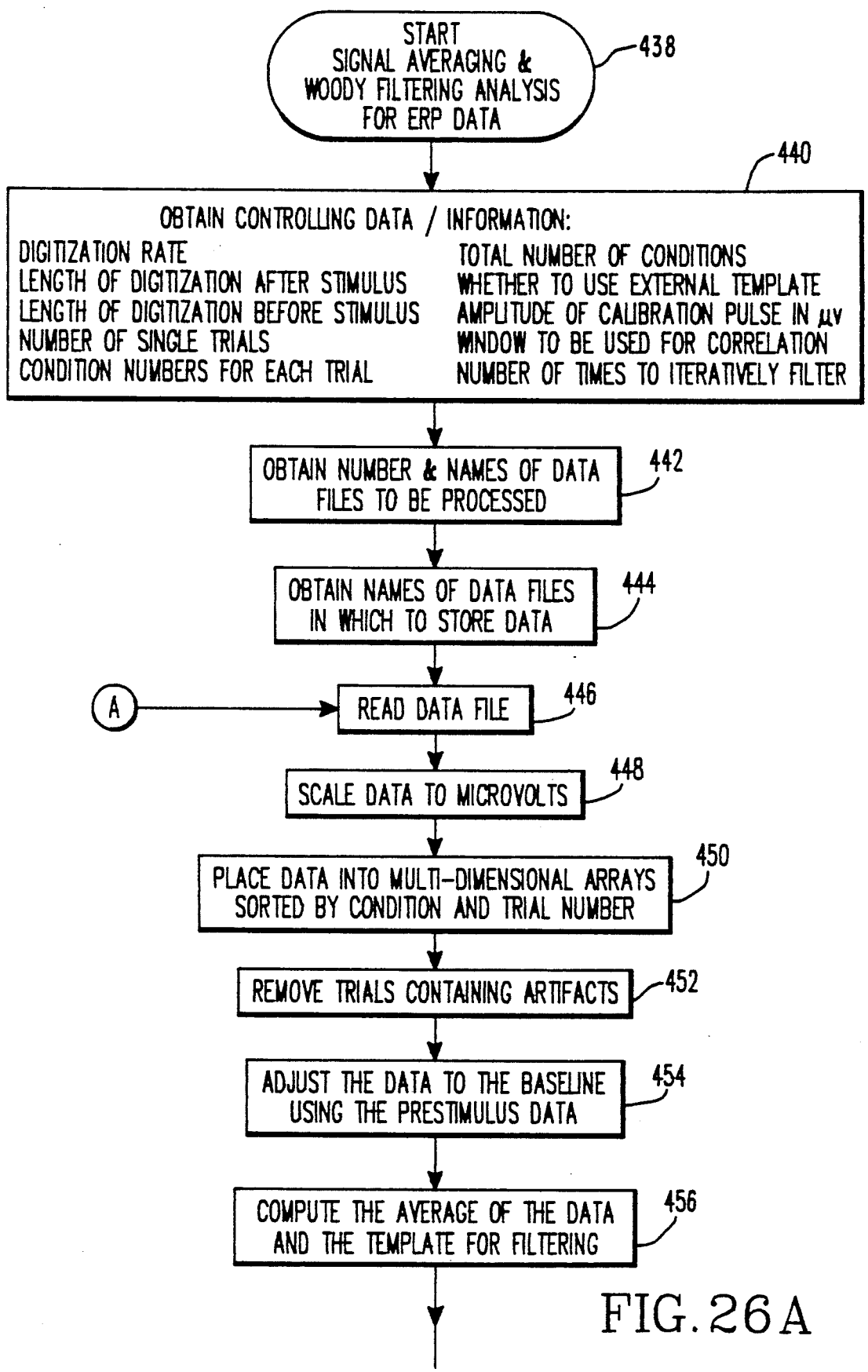
FIGS. 26A and 26B depict ERP signal analysis.
Figure 26B:
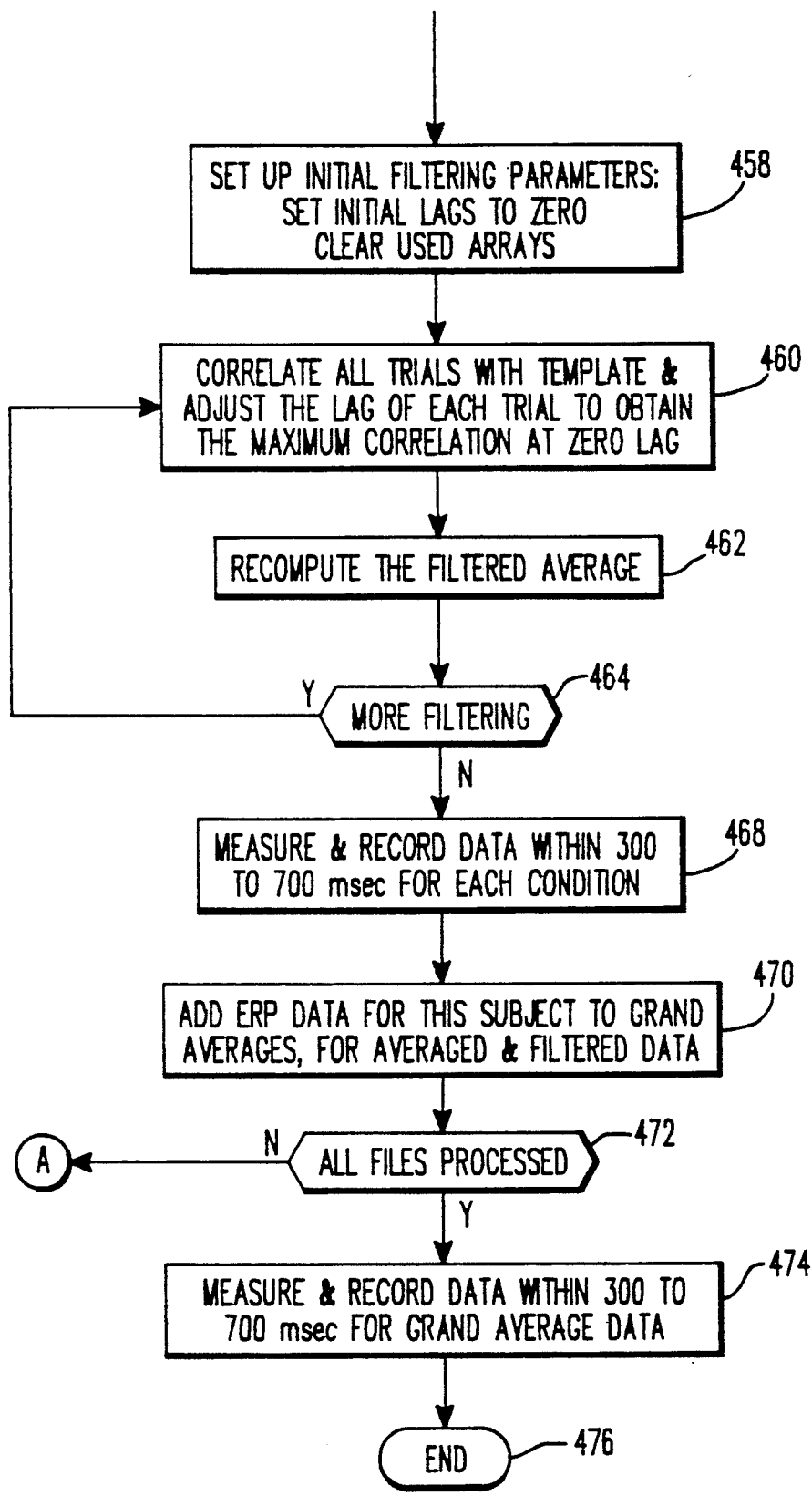

After the data is transferred to the signal analysis computer 205, the sequence of processing steps which produces the plots as previously discussed is illustrated in FIG. 24. First the EEG is analyzed 370 using a conventional FFT (Fast Fourier Transform routine) for the entire commercial and for the segments of the commercial. Based on the amplitude in the alpha and beta portions of the spectrum the amplitudes for the entire commercial are output 372 followed by plotting the alpha and beta amplitudes for the segments 374. The routine which performs the functions of blocks 370-374 is illustrated in FIGS. 25A and 25B. The ERP data can sometimes be contaminated with various types of noise and two types of signal filtering are performed on this data to remove the noise as illustrated in FIG. 24. First signal averaging for the ERP tests is performed 376 followed by adaptive filtering 378. If the latency of the ERP is necessary for the particular test, for example the value test, only the signal averaged data can be used to determine ERP amplitude and latency because adaptive filtering destroys latency information. If latency is not necessary it is possible to adaptively filter 378 the ERP data. After signal averaging and adaptive filtering the data is plotted 380. Adaptive filtering will positively enhance the data and thereby enhance the differences in peak amplitudes between various products, pictures and words. The adaptive filtering is chosen when latency is not necessary and when the averaged data and the adaptive filtered data do not diverge significantly. The divergence is determined by using standard statistical analysis techniques 382 to compare the amplitudes produced in both during signal averaging and adaptive filtering. Based on the results of the statistical test the adaptive filtered plots may be discarded as will be discussed in more detail later. FIGS. 26A-26C illustrate the software which performs the signal averaging, adaptive filtering and output.

The frequency analysis routine depicted in FIGS. 25A and 25B is described in more detail in the pseudo code of Appendix 3. This routine uses a standard decimation in time frequency algorithm such as can be found in Burrus and Parks, DFT/FFT and Convolution Algorithms, Wiley, 1985. After the frequency analysis routine is started 400 the control data is obtained 402 followed by obtaining 404 the number and names of data files to be processed and obtaining 406 the names of data files in which the output data is to be stored. This information is supplied by the user. Next the data is read 408 followed by a scaling 410 of the data to a microvolt level. The DC component is removed from the data followed by an execution 414 of the FFT routine for the entire recorded EEG for each subject. This routine displays the FFT data for the entire data set. Next the EEG data is divided 416 into the requested intervals and the DC component is removed 418 from each interval followed by another call of the FFT routine for each interval along with a display of the resultant data 420. The amplitude data is then measured and recorded 422 for the entire EEG and for the EEG intervals. The interval data is added to the grand averages after which it is determined 426 whether all the data files have been processed. If so the final data is displayed 428.

The signal averaging and adaptive filtering routine is illustrated in FIGS. 26A-26C and the details of this routine are provided in Appendix 4. This program computes the brain activity using two different techniques, signal averaging and adaptive or Woody filtering. A discussion of the Woody filtering algorithm can be found in Woody, Characterization of an Adaptive Filter for the Analysis of Variable Components, Med Biol Eng., 5, 539-553, 1967. Signal averaging is the straightforward method of averaging together all the ERPs of each condition. With the Woody filtering technique, a template specified by the user is correlated with all of the ERPs (single trials) of each condition. The ERPs are then time shifted so that each one has a maximum correlation with the template at zero lag. The Woody filtered signal is the average of the time adjusted ERPs.

The user chooses one of two methods for determining a template for the Woody filtering. A triangular or rounded triangular wave centered at 375 milliseconds after a stimulus presentation can be used as the template. The correlation between this template and each single trial is done once and a filtered signal for each condition is the time adjusted average of the single trials and each condition. A template for each condition can also be the time adjusted average of all single trials within that condition. This is an adaptive method which involves computing the template, correlating all ERPs with the template for each condition and time shifting accordingly and repeating this process. The initial template is the average of the non-adjusted ERPs.

Because cf the different ways in which the brain responds to different conditions presented and the needs of the different tests, the method of measuring the brain activity and the signals vary. The program uses two methods of determining results: 1) determining the maximum peak amplitude within a specified window and 2) determining the latency of the maximum peak within a specified window. These measurement techniques are used to compute the brain activity in both the averaged and filtered data.

The program illustrated in FIG. 26 will read the ERP data, calculate and display the averaged and filtered ERP for each condition and measure and record the brain activity for each condition. The program accepts one data file per subject and can process an infinite number of data files. The program also computes a "grand average" of the averaged and filtered ERPs for all subjects processed when the program is run.

The program starts, as illustrated in FIG. 26A, by obtaining 440 the controlling data and the input 442 and output 444 files. Next the data is read 446, scaled 448 and placed into multi-dimensional arrays 450 according to condition and trial number. Next the program removes 452 all trials containing artifact data and then adjusts 454 all the data using the base line data collected during the interval between the record pulse and the time at which the stimulus is presented. Next the data average and the template for the data are computed 456 followed by setting up 458 the initial filter parameters. The trials are circularly correlated with a template with a limit of 250 milliseconds on the shift allowed during correlation and the lag of each trial is obtained 460. The recomputed filter average is next produced 462 followed by a determination 464 as to whether additional filtering is necessary. If additional filtering is not necessary the data within the ERP window is measured 468 for peak value and the data is added 470 to the data for this subject. If all files have been processed 472 then the data is measured and recorded 474 for the grand average.

As previously mentioned once the outputs are produced for the adaptive filtered data and the signal averaged data, a determination must be made concerning which amplitude outputs are to be used. To make this determination first, the signal averaged data are statistically analyzed using an analysis of variance test using a package such as the BMDP available for am IBM AT. Next the Woody filtered data are statistically analyzed using the analysis of variance test. Before the adaptively filtered data is used as the output for amplitude measurements, the following conditions must be met: (1) the adaptively filtered data must generate the same pattern of results as the signal averaged data; and (2) the adaptively filtered data must be more statistically reliable, that is, the error variance must be lower. If these conditions are not met then the signal averaged data is reported as the final output. As an example of condition (1) assume that data are collected for four words presented as stimuli W1, W2, W3 and W4 and the signal averaged data show that responses to W1 and W2 are both larger than W3 and W4 and that the adaptively filtered data show that responses to W3 and W4 are larger than the responses to W1 and W2. In this case, since the pattern of results is completely different for the adaptive filtered data the adaptive filtered data output graphs would not be used. Condition 2 is satisfied if the adaptive filtering results in data that have a treatment variance that is larger relative to the error variance than the signal averaged data. This would translate into a more powerful statistical test. The adaptively filtered data usually will not satisfy conditions 1 and 2 when the data is noisy.

In the above-discussion, the invention can use conventional non-polarizing electrodes to obtain the signal samples from the subject, however, as advances in magnetoencephalography decrease the size and increase the sensitivity of remote sensors, they would be a good candidate for non-contact sensors for use in this invention.

The many features and advantages of the invention are apparent from the detailed specification and, thus, it is intended by the appended claims to cover all such features and advantages of the invention which fall within the true spirit and scope thereof. Further, since numerous modifications and changes will readily occur to those skilled in the art, it is not desired to limit the invention to the exact construction and operation illustrated and described, and accordingly all suitable modifications and equivalents may be resorted to, falling within the scope of the invention.

We claim as our Invention:

1. A method of evaluating a television advertisement having an advertisement object presented to a subject, comprising the steps of:
   (a) presenting the advertisement to the subject;
   (b) evoking event related potential brain activity responses by the subject to test materials related and not related to the advertisement, the test materials including an image of the object, content statements about the advertisement, price statements about the object and willingness to purchase statements about the object; and
   (c) analyzing the evoked event related potential brain activity responses by determining position and amplitude of peaks in the event related potential brain activity responses to determine and indicate understanding of the advertisement, value of the object and commitment to the object.

2. A method as recited in claim 1, further comprising the steps of:
   (d) digitally recording brain activity of the subject during the advertisement; and
   (e) analyzing the brain activity to determine one of attention to and cognition of the advertisement.

3. A method as recited in claim 2, wherein step (d) includes recording electroencephalographic brain activity and step (e) comprises measuring an amplitude of a predetermined frequency component.

4. A method as recited in claim 3, wherein step (e) further comprises measuring the amplitude of segments of the brain activity and for the entire recorded brain activity.

5. A method as recited in claim 4, wherein the predetermined frequency component comprises one of alpha and beta frequency components.

6. A method as recited in claim 1, wherein step (b) includes recording evoked potentials produced by the subject and step (c) comprises measuring one of amplitude or latency of predetermined components of the evoked potentials.

7. A method as recited in claim 6, wherein step (b) includes:
   (b1) printing the subject; and
   (b2) presenting a stimulus to the subject.

8. A method as recited in claim 6, wherein step (b) includes presenting to the subject one of advertisement images and advertisement words.

9. A method of evaluating a first television advertisement having an advertisement object presented to a subject, comprising the steps of:
   (a) presenting first film entertainment material to the subject;
   (b) presenting the first advertisement to the subject and recording electroencephalographic activity of the subject during the first advertisement;
   (c) presenting a second advertisement to the subject;
   (d) presenting second film entertainment material to the subject;
   (e) presenting the subject with visual test materials related and not related to the first advertisement and digitally recording evoked event related potentials produced by the subject, the test materials including an image of the object, content statements about the first advertisement, price statements about the object and willingness to purchase statements about the object;
   (f) digitally measuring amplitudes of predetermined frequency components of the electroencephalographic activity in segments of and overall for the recorded electroencephalographic activity;
   (g) measuring amplitude of late components of the evoked event related potentials;
   (h) measuring latency of late components of the evoked event related potentials; and
   (i) determining understanding of the first advertisement, value of the object and commitment to the object using the amplitude and latency where understanding is determined from the amplitude and latency produced by the content statements and value from the amplitude and latency produced by the price statements and commitment from the amplitude and latency produced by the purchase statements.

10. An apparatus for evaluating a television advertisement having an object presented to a statement, comprising:
    signal recording means for recording evoked event related potential evoked brain activity of the subject during tests following the advertisement, the test including pictures of the object, content statements about the advertisement, price statements about the object and willingness to purchase statements about the object; and
    signal analysis means for analyzing the evoked event related potential evoked brain activity by determining position and amplitude of peaks in the event related potential brain activity to determine and indicate understanding of the advertisement, value of the object and commitment to the object, where understanding is determined by the activity produced by the content statements, value by the activity produced by the price statements and commitment by the activity produced by the purchase statements.

11. An apparatus as recited in claim 10, further comprising initiation means for starting recording.

12. An apparatus as recited in claim 10, wherein said signal recording means records brain activity during the advertisement and said signal analysis means determines attention to and cognition of the advertisement from the brain activity recorded during the advertisement.

13. An apparatus as recited in claim 12, wherein said signal analysis means includes frequency means for determining amplitude of predetermined frequency components in the activity recorded during segments of the advertisement and over the entire advertisement.

14. An apparatus as recited in claim 10, wherein said signal analysis means comprises latency means for determining amplitude and latency of predetermined components in the evoked brain activity.

15. An apparatus for evaluating a television advertisement having an object presented to a subject, comprising:
  a video tape player presenting the advertisement and test materials including images of the object, content statements about the advertisement, price statements about the object and willingness to purchase statements about the object, and producing a record start signal;
  a converter connected to said player and converting the record start signal into a record pulse;
  sensors for sensing brain wave signals;
  an amplifier/filter unit connected to said sensors for amplifying and filtering the brain wave signals;
  an analog to digital conversion unit connected to said amplifier/filter unit, having a digital output connected to said converter and for converting the brain wave signals;
  a recording computer connected to said conversion unit and said player for recording the signals responsive to the record pulse; and
  a signal analysis computer receiving the recorded signals, determining attention to and cognition of segments of the advertisement and the overall advertisement by measuring amplitudes of alpha and beta frequency components produced during the segments and overall, and determining understanding of the advertisement, commitment to objects in the advertisement and value of objects in the advertisement by measuring amplitude and latency of late evoked event related potentials in the recorded signal, with understanding being determined by the potentials produced when the content statements about the advertisement are presented to the subject, value being determined by the potentials produced when the price statements about the object are presented to the subject and commitment being determined by the potentials produced when the purchase statements about the object are presented to the subject.

16. A method of evaluating a television advertisement having an advertisement object presented to a subject, comprising the steps of:
  (a) presenting the advertisement to the subject;
  (b) recording evoked event related potential brain activity responses by the subject to test materials related and not related to the advertisement, the test materials including an image of the object, pictures from the advertisement, content statements about the advertisement, price statements about the object and willingness to purchase statements about the object; and
  (c) analyzing the evoked event related potential brain activity responses by determining position and amplitude of peaks in the event related brain activity responses to determine and indicate awareness of the advertisement, understanding of the advertisement, value of the object and commitment to the object.

* * * * *